United States Patent
Fuketa et al.

(10) Patent No.: US 10,413,247 B2
(45) Date of Patent: Sep. 17, 2019

(54) SIGNAL DETECTION DEVICE, SIGNAL DETECTION METHOD, AND METHOD OF MANUFACTURING SIGNAL DETECTION DEVICE

(71) Applicant: Japan Science and Technology Agency, Kawaguchi-shi, Saitama (JP)

(72) Inventors: Hiroshi Fuketa, Tsukuba (JP); Makoto Takamiya, Tokyo (JP); Takayasu Sakurai, Tokyo (JP); Tsuyoshi Sekitani, Osaka (JP); Takao Someya, Tokyo (JP)

(73) Assignee: JAPAN SCIENCE AND TECHNOLOGY AGENCY, Kawaguchi-Shi (JP)

( * ) Notice: Subject to any disclaimer, the term of this patent is extended or adjusted under 35 U.S.C. 154(b) by 1058 days.

(21) Appl. No.: 14/767,976

(22) PCT Filed: Feb. 14, 2014

(86) PCT No.: PCT/JP2014/053548
§ 371 (c)(1),
(2) Date: Aug. 14, 2015

(87) PCT Pub. No.: WO2014/126223
PCT Pub. Date: Aug. 21, 2014

(65) Prior Publication Data
US 2016/0007927 A1    Jan. 14, 2016

(30) Foreign Application Priority Data
Feb. 15, 2013  (JP) ................................ 2013-028289

(51) Int. Cl.
*A61B 5/0492*   (2006.01)
*A61B 5/0488*   (2006.01)
(Continued)

(52) U.S. Cl.
CPC .......... *A61B 5/7203* (2013.01); *A61B 5/0492* (2013.01); *A61B 5/04888* (2013.01);
(Continued)

(58) Field of Classification Search
CPC . A61B 5/7203; A61B 5/7225; A61B 5/04012; A61B 2562/046
See application file for complete search history.

(56) References Cited

U.S. PATENT DOCUMENTS 5,483,967 A    1/1996  Ohtake
2006/0270942 A1*  11/2006  McAdams .......... A61B 5/0531
                                                  600/547
(Continued)

FOREIGN PATENT DOCUMENTS

CN    101282684 A    10/2008
JP    H06-197877 A    7/1994
(Continued)

OTHER PUBLICATIONS

Yokota, et al. "Sheet-Type Flexible Organic Active Matrix Amplifier System Using Pseudo-CMOS Circuits With Floating-Gate Structure" IEEE Trans. on Electron Devices; v.59 No. 12; pp. 3434-3441 (2012).*
(Continued)

*Primary Examiner* — Lee S Cohen
*Assistant Examiner* — Erin M Cardinal

(57) ABSTRACT

A signal detection device includes: multiple electrodes that are arranged to come into contact with a subject that generates a signal; an electrode signal selection unit that alternatively selects one signal from signals on the multiple electrodes based on a selection signal; an amplification unit that amplifies the signal that is selected by the electrode signal selection unit; and a flexible substrate on which the multiple electrodes, the selection unit, and the amplification
(Continued)

unit are formed, in which the amplification unit is formed on the substrate to form a laminated structure together with the multiple electrodes and the selection unit.

8 Claims, 12 Drawing Sheets

(51) Int. Cl.
  *A61B 5/00* (2006.01)
  *A61B 5/04* (2006.01)
(52) U.S. Cl.
  CPC .......... *A61B 5/6832* (2013.01); *A61B 5/7225* (2013.01); *A61B 5/04012* (2013.01); *A61B 5/0488* (2013.01); *A61B 5/4851* (2013.01); *A61B 2562/0209* (2013.01); *A61B 2562/0214* (2013.01); *A61B 2562/046* (2013.01); *A61B 2562/125* (2013.01); *A61B 2562/164* (2013.01); *A61B 2562/222* (2013.01)

(56) References Cited

U.S. PATENT DOCUMENTS

| | | | |
|---|---|---|---|
| 2009/0177144 A1* | 7/2009 | Masmanidis | A61B 5/04001 604/66 |
| 2010/0016702 A1* | 1/2010 | Greene | A61B 5/0408 600/391 |
| 2010/0298895 A1* | 11/2010 | Ghaffari | A61B 1/00082 607/3 |
| 2011/0054583 A1* | 3/2011 | Litt | A61B 5/0031 607/116 |
| 2013/0041235 A1 | 2/2013 | Rogers | |
| 2013/0072775 A1* | 3/2013 | Rogers | A61B 5/0478 600/378 |
| 2013/0333094 A1* | 12/2013 | Rogers | A61B 5/01 2/161.7 |
| 2015/0276430 A1* | 10/2015 | Sekitani | A61B 5/0478 324/609 |

FOREIGN PATENT DOCUMENTS

| | | |
|---|---|---|
| JP | H06-245915 A | 9/1994 |
| JP | 2004-267298 A | 9/2004 |
| JP | 2008-086392 A | 4/2008 |
| JP | 2011-513038 A | 4/2011 |
| WO | 2009/114689 A1 | 9/2009 |

OTHER PUBLICATIONS

State Intellectual Property Office of the People's Republic of China, "Office Action and Search Report," issued in CN Patent Application No. 2014800188748, which is a Chinese counterpart of U.S. Appl. No. 14/767,976, dated Jan. 23, 2017, 9 pages (3 pages of English translation of Search Report, and 3 pages of Search Report and 3 pages of Office Action).
Tomoyuki Yokota et al., "Sheet-Type Flexible Organic Active Matrix Amplifier System Using Pseudo-CMOS Circuits With Floating-Gate Structure," IEEE Transactions on Electron Devices, vol. 59, Issue 12, pp. 3434-3441 (Dec. 2012), IEEE.
Tomoyuki Yokota et al., "Sheet-type Organic Active Matrix Amplifier System using Vth-Tunable, Pseudo-CMOS Circuits with Floating-gate Structure", IEEE International Electron Devices Meeting, pp. 14.4.1-14.4.4 (Dec. 2011).
Pu Liu et al., "EMG-to-Force Modeling for Multiple Fingers", IEEE Annual Northeast Bioengineering Conference (NEBEC), pp. 1-2 (Apr. 2011).
Didier Staudenmann et al., "Towards optimal multi-channel EMG electrode configurations in muscle force estimation: a high density EMG study", Journal of Electromyography and Kinesiology, vol. 15, Issue 1, pp. 1-11 (Feb. 2005), Elsevier Ltd.
B. G. Lapatki et al., "A thin, flexible multielectrode grid for high-density surface EMG", Journal of Applied Physiology, vol. 96, No. 1, pp. 327-336 (Jan. 2004), the American Physiological Society.
Tatsuya Yamamoto and Kazuo Takimiya, "Facile Synthesis of Highly Π-Extended Heteroarenes, Dinaphtho[2,3-b:2',3'-f]chalcogenopheno[3,2-b]chalcogenophenes, and Their Application to Field-Effect Transistors", Journal of the American Chemical Society, vol. 129, No. 8, pp. 2224-2225 (Aug. 2007).
Hagen Klauk et al., "Ultralow-power organic complementary circuits", Nature, vol. 445, pp. 745-748 (Feb. 15, 2007), Nature Publishing Group.
Koichi Ishida et al., "100V AC Power Meter System-on-a-Film (SoF) Integrating 20V Organic CMOS Digital and Analog Circuits with Floating Gate for Process-Variation Compensation and 100V Organic PMOS Rectifier", IEEE International Solid-State Circuits Conference Digest of Technical Papers (ISSCC), pp. 218-220 (Feb. 2011).
Hagen Marien et al., "A Fully Integrated ΔΣ ADC in Organic Thin-Film Transistor Technology on Flexible Plastic Foil", IEEE Journal of Solid-State Circuits, vol. 46, No. 1, pp. 276-284 (Jan. 2011).
International Search Report received for PCT Patent Application No. PCT/JP2014/053548 dated Apr. 8, 2014, 4 pages (2 pages of English Translation of International Search Report, 2 pages of International Search Report).
European Patent Office, "Extended European Search Report," issued in European Patent Application No. 14 751 773.4, which is a European counterpart of U.S. Appl. No. 14/767,976, dated Sep. 7, 2016, 10 pages.
Hiroshi Fuketa et al., "1[mu]m-thickness 64-channel surface electromyogram measurement sheet with 2V organic transistors for prosthetic hand control", Solid-State Circuits Conference Digest of Technical Papers (ISSCC), 2013 IEEE International, IEEE, Feb. 17, 2013 (Feb. 17, 2013), pp. 104-105, XP032350493, DOI: 10.1109/ISSCC.2013.6487656 ISBN: 978-1-4673-4515-6.
Jium-Ming Lin et al., "Integrating micro array bio-sensing probes with semiconductor amplifier on a flexible substrate", Sensing Technology, 2008, ICST 2008, 3rd International Conference on, IEEE, Piscataway, NJ, USA, Nov. 30, 2008 (Nov. 30, 2008), pp. 76-81, XP031918105, DOI: 10.1109/ICSENST.2008.4757077, ISBN: 978-1-4244-2176-3.
Takao Someya et al., "Ultraflexible Organic Devices for Biomedical Applications", 2013 IEEE International Electron Devices Meeting, Dec. 9-11, 2013, Washington, DC, USA, Dec. 1, 2013 (Dec. 1, 2013), pp. 8.5.1-8.5.4, XP055298696, DOI: 10.1109/IEDM.2013.6724588 ISBN: 978-1-4799-2306-9.

* cited by examiner

| SUMMARY OF CHARACTERISTICS OF AMPLIFIER | | |
|---|---|---|
| −3dB frequency | | 60Hz |
| GAIN | @10Hz | 27dB |
| | @100Hz | 21dB |
| | @200Hz | 17dB |
| | @500Hz | 10dB |

| ORGANIC TRANSISTOR | |
|---|---|
| SEMICONDUCTOR MATERIAL | DNTT (MOBILITY=1.0cm2/Vs) |
| MATERIAL OF GATE OXIDATION FILM, THICKNESS | SAM 2nm+AlO×4nm=6nm |
| MINIMUM GATE LENGTH | 20μm |
| SURFACE ELECTROMYOGRAM MEASUREMENT SHEET | |
| SHEET SIZE | 45mm×40mm |
| NUMBER OF AMPLIFIERS | 16 |
| NUMBER OF EMG ELECTRODES | 8×8 (5mm PITCH) |

SIGNAL DETECTION DEVICE, SIGNAL DETECTION METHOD, AND METHOD OF MANUFACTURING SIGNAL DETECTION DEVICE

CROSS REFERENCE TO RELATED APPLICATIONS

This patent application is a U.S. national stage application under 35 U.S.C. § 371 of International Patent Application No. PCT/JP 2014/053548filed on Feb. 14, 2014, which claims the benefit of foreign priority to Japanese Patent Application No. JP 2013-028289filed on Feb. 15, 2013. The International Application was published in Japanese on Aug. 21, 2014, as International Publication No. WO 2014/126223A1 under PCT Article 21(2).

BACKGROUND OF THE INVENTION

Field of the Invention

The present invention relates to a signal detection device for detecting a signal, a signal detection method, and a method of manufacturing the signal detection device.

Priority is claimed on Japanese Patent Application No. 2013-028289, filed Feb. 15, 2013, the content of which is incorporated herein by reference.

Description of Related Art

In the related art, for example, as devices for detecting a biological signal, signal detection devices such as an electrocardiograph and electroencephalograph are known (PTL 1). Normally, in this type of signal detection device, a difference between signals of a pair of electrodes that are mounted on a living body that is a subject is amplified with a differential amplifier, and thus a noise component in the same phase that is included in the signals is canceled out and a detection signal having a high SN ratio is obtained.

CITATION LIST

Patent Literature

[PTL 1] Japanese Unexamined Patent Application, First Publication No. H6-197877.

Non-Patent Literature

[NPL 1]T. Yokota, et al., "Sheet-Type Organic Active Matrix Amplifier System Using Vth-Tunable, Pseudo-CMOS Circuits with Floating-Gate Structure," IEEE International Electron Devices Meeting, pp. 335-338, December 2011.

SUMMARY OF THE INVENTION

However, according to the technologies in the related art, because an electrode and a differential amplifier are connected to each other through a wiring cable, there is a likelihood that noise will infiltrate into a wiring cable and there is a limitation to an improvement in an SN ratio of a detection signal. Furthermore, although the electrode and the differential amplifier are integrated into one piece, it is difficult to arrange electrodes in a two-dimensional form with a high density. For this reason, it is difficult to acquire a distribution of a biological signal with high precision.

As a technology relating to a signal detection device that has electrodes which are arranged in a two-dimensional form, there is a technology that stacks multiple electrodes and multiple amplifiers on a substrate in the form of a sheet (NPL 1). However, according to this technology, because there is a need to arrange an amplifier in every electrode, although only the electrode is miniaturized, in terms of arrangement of the amplifiers, an arrangement pitch between the electrodes is limited and there is a limitation to an improvement of an electrode density.

An object of the present invention, which is made in view of the situation described above, is to provide a signal detection device, a signal detection method, and a method of manufacturing the signal detection device, in all of which an SN ratio of a detection signal is capable of being improved and electrodes are capable of being arranged at a high density.

In order to solve the problems described above, according to an aspect of the present invention, there is provided a signal detection device including: multiple electrodes that are arranged to come into contact with a subject that generates a signal; a selection unit that alternatively selects one signal from signals on the multiple electrodes based on a selection signal; an amplification unit that amplifies the signal that is selected by the selection unit; and a flexible substrate on which the multiple electrodes, the selection unit, and the amplification unit are formed, in which the amplification unit is formed on the substrate to form a laminated structure together with the multiple electrodes and the selection unit.

In the signal detection device described above, for example, the selection unit may be configured from multiple source follower circuits that correspond to the multiple electrodes, respectively, and one of the source follower circuits alternatively selected from the multiple source follower circuits based on the selection signal may be activated.

In the signal detection device described above, for example, each of the multiple source follower circuits may include a first transistor, the gate of which is connected to any of the electrodes, and the drain of which is connected to a predetermined fixed potential node, and a second transistor that is connected between the source of the first transistor and a load electric current source, the selection signal being supplied to the gate of the second transistor.

In the signal detection device described above, for example, the amplification unit may include a capacitor that has a first electrode that is commonly connected to output parts of the multiple source follower circuits, and an amplifier, an input part of which is connected to a second electrode of the capacitor.

In the signal detection device described above, for example, the amplification unit may include a transistor group for adjusting the electrical characteristics of the amplifier, and one or several transistors that constitute the transistor group may be selectively connected in parallel to each other to obtain desired electrical characteristics.

For example, the signal detection device described above may include multiple blocks that are arranged in the form of a matrix, and in which one block is made from the multiple electrodes, the selection unit, and the amplification unit, and may further include a selection unit for selecting an output signal of the amplification unit, which is provided to each of the multiple blocks.

In order to solve the problems described above, according to another aspect of the present invention, a signal detection method is provided including: a selection step of causing a selection unit to select one signal alternatively from signals on multiple electrodes that are arranged to come into contact with a subject that generates a signal, based on a selection signal; and an amplification step of causing an amplification unit to amplify the signal selected by the selection unit in the selection step, in which the multiple electrodes, the selection unit, and the amplification unit are formed on a flexible substrate, and in which the amplification unit is formed on the substrate to form a multi-layer structure together with the multiple electrodes and the selection unit.

In order to solve the problems described above, according to another aspect of the present invention, a method of manufacturing a signal detection device is provided, which includes multiple electrodes that are arranged to come into contact with a subject that generates a signal, a selection unit that alternatively selects one signal from signals on the multiple electrodes, based on a selection signal, an amplification unit that amplifies the signal that is selected by the selection unit, and a substrate having flexibility, on which the multiple electrodes, the selection unit, and the amplification unit are formed, the method including a step of forming the multiple electrodes and the selection unit on the substrate; and a step of forming the amplification unit on the substrate to form a laminated structure together with the multiple electrodes and the selection unit.

According to the aspects of the present invention, because multiple electrodes that are arranged in two dimensions and an amplifier is stacked and the multiple electrodes are configured to selectively connect with the amplifier, an SN ratio of a detection signal can be improved, and the multiple electrodes can be arranged in a high density.

DETAILED DESCRIPTION OF THE INVENTION

Description of a Configuration

Figure 1:
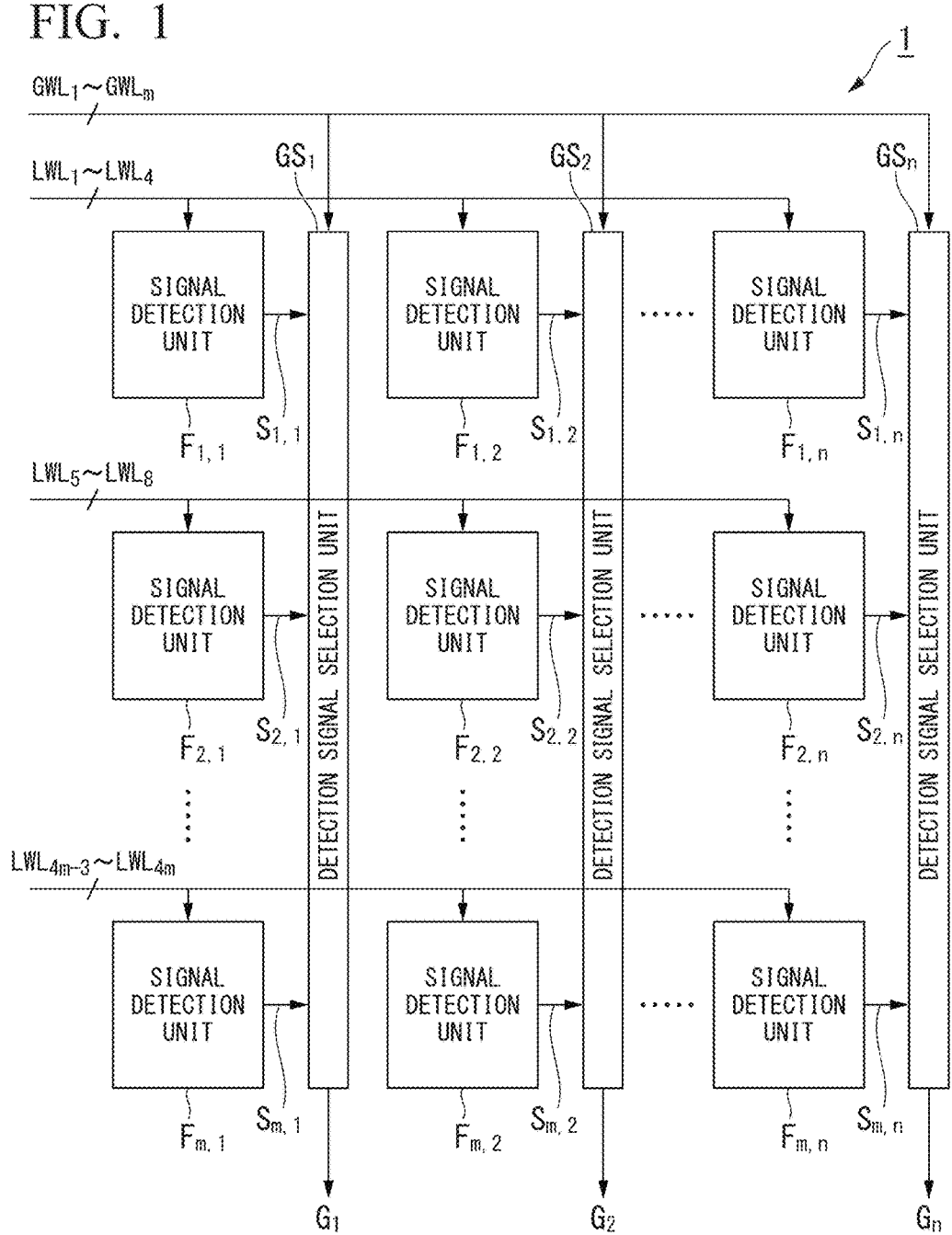
FIG. 1 is a block diagram that schematically illustrates a configuration example of a signal detection device according to an embodiment of the present invention.

FIG. 1 is a block diagram that schematically illustrates a configuration example of a signal detection device 1 according to an embodiment of the present invention. The signal detection device 1 according to the present embodiment detects a weak electrical signal that originates from a subject such as a living body. The signal detection device 1 includes multiple signal detection units $F_{1,1}$ to $F_{m,n}$ that are arranged in the form of a m row×n column matrix (m and n are natural numbers equal to or greater than 2), multiple detection signal selection units $GS_1$ to $GS_n$, multiple local word lines $LWL_1$ to $LWL_{4m}$, and multiple global word lines $GWL_1$ to $GWL_m$. The signal detection units $F_{1,1}$ to $F_{m,n}$ detect a biological signal that is generated by the subject and amplifies the biological signal. Each of the signal detection units $F_{1,1}$ to $F_{m,n}$, as described below, includes four electrodes and is configured to selectively amplify the biological signal that is input through each electrode. The detection signal selection units $GS_1$ to $GS_n$ select signals for one row, among detection signals $S_{1,1}$ to $S_{m,n}$ that are detected by the signal detection units $F_{1,1}$ to $F_{m,n}$ respectively, and output the selected signals as output signals $G_1$ to $G_n$, respectively.

The signal detection units $F_{1,1}$ to $F_{m,n}$, the detection signal selection units $GS_1$ to $GS_n$, the local word lines $LWL_1$ to $LWL_{4m}$, the global word lines $GWL_1$ to $GWL_m$, the detection signals $S_{1,1}$ to $S_{m,n}$, and the output signals $G_1$ to $G_n$ are hereinafter collectively referred to as reference characters "F," "GS," "LWL," "GWL," "S," and "G," respectively.

Moreover, according to the present embodiment, a living body is assumed to be the subject, but the signal detection device 1 according to the present embodiment can detect a weak electrical signal that originates from an arbitrary object as the subject which is not limited to a living body. For example, the signal detection device 1 can be also applied for the purpose of detecting a signal distribution on the surface of a manufactured product, an electric potential distribution in a liquid or space, or the like.

Among the signal detection units $F_{1,1}$ to $F_{m,n}$ that are arranged in the form of a matrix, each output part of the signal detection units $F_{1,1}$ to $F_{m,1}$ in a first column is connected to the detection signal selection unit $GS_1$, and each output part of the signal detection units $F_{1,2}$ to $F_{m,2}$ in a second column is connected to the detection signal selection unit $GS_2$. The same manner applies subsequently. That is, each output part of the signal detection units $F_{1,n}$ to $F_{m,n}$ in an n-th column is connected to the detection signal selection unit $GS_n$. The multiple global word lines $GWL_1$ to $GWL_m$ are commonly connected to the detection signal selection units $GS_1$ to $GS_n$. Among these, the global word line $GWL_1$ is for selecting the detection signals $S_{1,1}$ to $S_{1,n}$ that are output from the signal detection units $F_{1,1}$ to $F_{1,n}$ in a first row, respectively. The global word line $GWL_2$ is for selecting the detection signals $S_{211}$ to $S_{2,n}$ that are output from the signal detection units $F_{2,1}$ to $F_{2,n}$ in a second row, respectively. The same manner applies subsequently. That is, the global word line $GWL_m$ is for selecting the detection signals $S_{m,1}$ to $S_{m,n}$ that are output from the signal detection units $F_{m,1}$ to $F_{m,n}$ in an m-th row, respectively.

Furthermore, among the signal detection units $F_{1,1}$ to $F_{m,n}$ that are arranged in the form of a matrix, the local word lines $LWL_1$ to $LWL_4$ are commonly connected to the signal detection units $F_{1,1}$ to $F_{1,n}$ in the first row, and the local word lines $LWL_5$ to $LWL_8$ are commonly connected to the signal detection units $F_{2,1}$ to $F_{2,n}$ in the second row. Similarly to the above, the local word lines $LWL_{4m-3}$ to $LWL_{4m}$ are commonly connected to the signal detection units $F_{m,1}$ to $F_{m,n}$ in an m-th row. The local word lines $LWL_1$ to $LWL_{4m}$ are for selecting the four electrodes that are included in the signal detection unit F and will be described in detail below.

Figure 2:
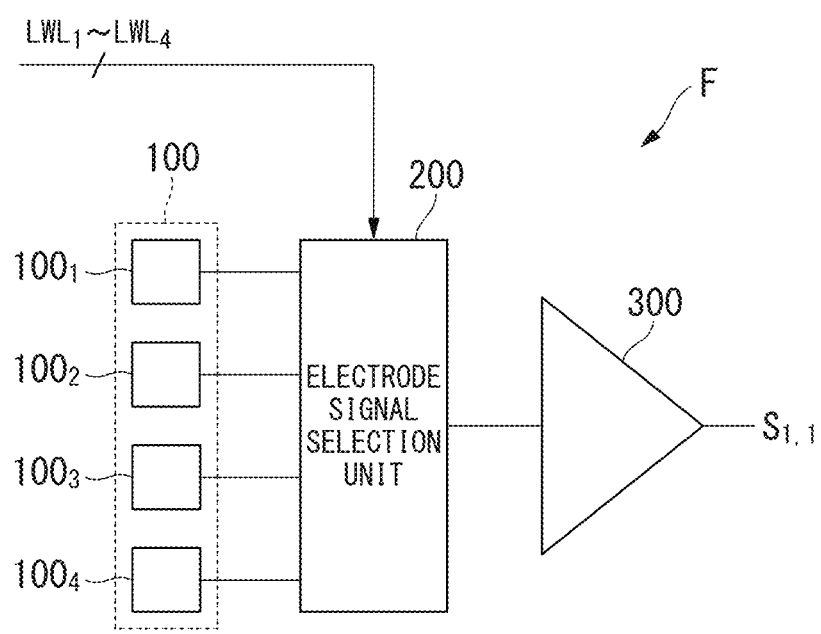
FIG. 2 is a block diagram illustrating a configuration example of a signal detection unit that is included in the signal detection device according to the embodiment of the present invention.

FIG. 2 is a block diagram illustrating a configuration example of the signal detection unit $F_{1,1}$ that is illustrated in FIG. 1.

According to the present embodiment, all the signal detection units $F_{1,1}$ to $F_{m,n}$ have the same configuration. As illustrated in FIG. 2, the signal detection unit $F_{1,1}$ includes an electrode group 100 that is made up of four electrodes $100_1$ to $100_4$, an electrode signal selection unit 200, and an amplification unit 300. The four electrodes $100_1$ to $100_4$ are arranged to come into contact with the subject (not illustrated) that generates the biological signal. The biological signal (the electrical signal) is applied from the subject to the electrodes $100_1$ to $100_4$. The biological signal is supplied, as an electrode signal, to the electrode signal selection unit 200 through an electrode.

Based on selection signals that are supplied through the local word lines $LWL_1$ to $LWL_4$, the electrode signal selection unit 200 alternatively selects one electrode signal from the electrode signals (the biological signals) that are input through the electrodes $100_1$ to $100_4$. Moreover, this example does not impose any limitation. The electrode signal selection unit 200 may select an arbitrary combination of biological signals on the electrodes $100_1$ to $100_4$. For example, all the biological signals on the electrodes $100_1$ to $100_4$ may be set to be selected by combining signal levels of the selection signals that are supplied through the local word lines $LWL_1$ to $LWL_4$. Furthermore, for example, a combination of the biological signal on the electrode $100_1$ and the biological signal on the electrode $100_3$ may be set to be selected. Furthermore, it is also possible to set all the biological signals on the electrodes $100_1$ to $100_4$ to be non-selected.

Figure 3:
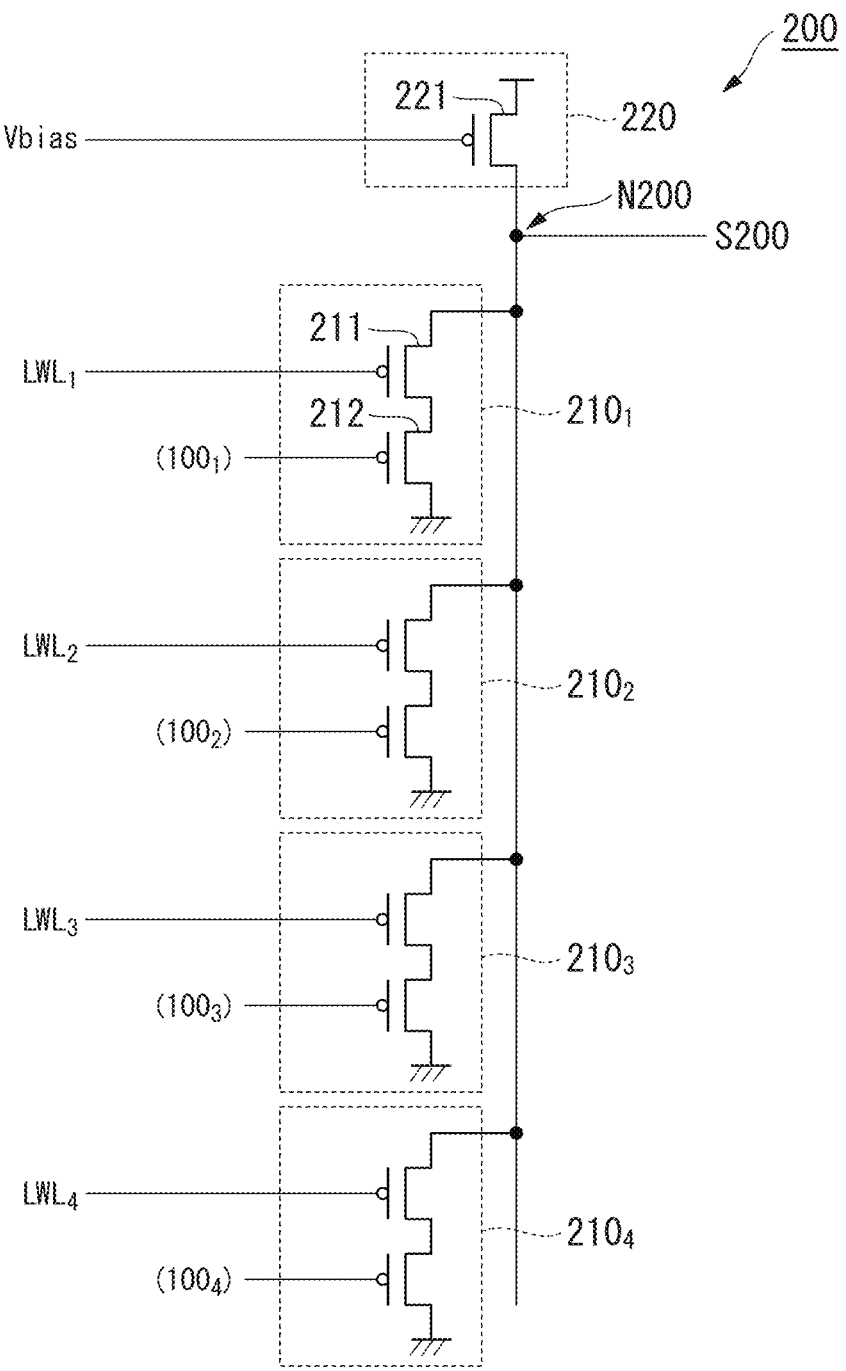
FIG. 3 is a circuit diagram illustrating a configuration example of an electrode signal selection unit that is included in a signal detection unit according to the embodiment of the present invention.

FIG. 3 is a circuit diagram illustrating a configuration example of the electrode signal selection unit 200. The electrode signal selection unit 200 is configured from four source follower circuits $210_1$ to $210_4$ that are provided to correspond to the four electrodes $100_1$ to $100_4$ that are illustrated in FIG. 2, respectively, and one load electric current source 220. Among these, the source follower circuit 210 is configured from pMOS transistors 211 and 212 that are organic transistors. Specifically, a source of the pMOS transistor 211 that constitutes the source follower circuit $210_1$ is connected to a node 200 that is an output part of the electrode signal selection unit 200, and the local word line $LWL_1$ is connected to a gate thereof. The drain of the pMOS transistor 211 is connected to a source of the pMOS transistor 212. The electrode 100 is connected to the gate of the pMOS transistor 212, and the drain thereof is connected to a predetermined fixed potential node (for example, a ground node). Moreover, the predetermined fixed potential node is not limited to the ground node, and is arbitrarily limited to a node that provide a potential that serves as a reference for detecting the biological signal, such as a case of the device or one portion of the subject.

Other source follower circuits $210_2$ to $210_4$ have the same configuration as the source follower circuit $210_1$ described above. However, among pMOS transistors that constitute the source follower circuits $210_2$ to $210_4$, local word lines $LWL_2$ to $LWL_4$ are connected to gates of transistors, respectively, that are equivalent to a pMOS 211 of the source follower circuit $210_1$ described above. Furthermore, among the pMOS transistors that constitute the source follower circuits $210_2$ to $210_4$, electrodes $100_2$ to $100_4$ are connected to gates of transistors, respectively; that are equivalent to the pMOS transistor 212 of the source follower circuit $210_1$ described above. For activation, one circuit is selected from among the source follower circuits $210_1$ to $210_4$ based on the selection signal that is supplied through the local word lines $LWL_1$ to $LWL_4$.

Moreover, according to the present embodiment, the electrode group 100 is configured from the four electrodes $100_1$ to $100_4$ and the four source follower circuits $210_1$ to $210_4$ that correspond to these electrodes $100_1$ to $100_4$, respectively, are provided, but this example does not impose any limitation. The number of electrodes that constitute the electrode group 100 is arbitrary, and the number of source follower circuits may be determined according to the number of electrodes.

The load electric current source 220 is configured from a pMOS transistor 221 that is an organic transistor. Specifically, a source of the pMOS transistor 221 that constitutes the load electric current source 220 is connected to a power supply node. A predetermined bias voltage Vbias is applied to a gate thereof. A bias voltage Vbias, for example, is set in such a manner that the pMOS transistor 221 operates in a saturation region. Accordingly, the pMOS transistor 221 functions as an approximately-constant current source. A drain of the pMOS transistor 221 is connected to a node N200 that is the output part of the electrode signal selection unit 200, along with each output part of the source follower circuits $210_1$ to $210_4$ described above. Accordingly, the load electric current source 220 functions as a load on the source follower circuits $210_1$ to $210_4$.

According to the present embodiment, like the electrode signal selection unit 200, biological signal selection units $GS_1$ to $GS_n$ that are illustrated in FIG. 1 are also configured to use a source follower circuit. However, biological signal selection units $GS_1$ to $GS_n$ each include m source follower circuits as elements that are equivalent to the four source follower circuits $210_1$ to $210_4$ that are illustrated in FIG. 3. Furthermore, in each of the m source follower circuits that are included in each of the biological signal selection units, any one of the global word lines ($GWL_1$ to $GWL_m$ is connected to the gate of a transistor that is equivalent to the pMOS transistor 211 in FIG. 3. Furthermore, in each of the m source follower circuits that are included in each of the biological signal selection units, any one of the detection signals S is supplied from the signal detection unit F to the gate of a transistor that is equivalent to the pMOS transistor 212 in FIG. 3. For example, in the biological signal selection unit GS1, any one of the detection signals $S_{1,1}$ to $S_{m,1}$ from the signal detection units $F_{1,1}$ to $F_{m,1}$ in a first column is supplied to the gate of a transistor that is equivalent to the pMOS transistor 212 in FIG. 3. This will be described in detail below in the following example.

Description is provided returning to FIG. 2. The output of the electrode signal selection unit 200 is connected to an input part of the amplification unit 300. The amplification unit 300 amplifies the biological signal that is selected by the electrode signal selection unit 200.

Figure 4:
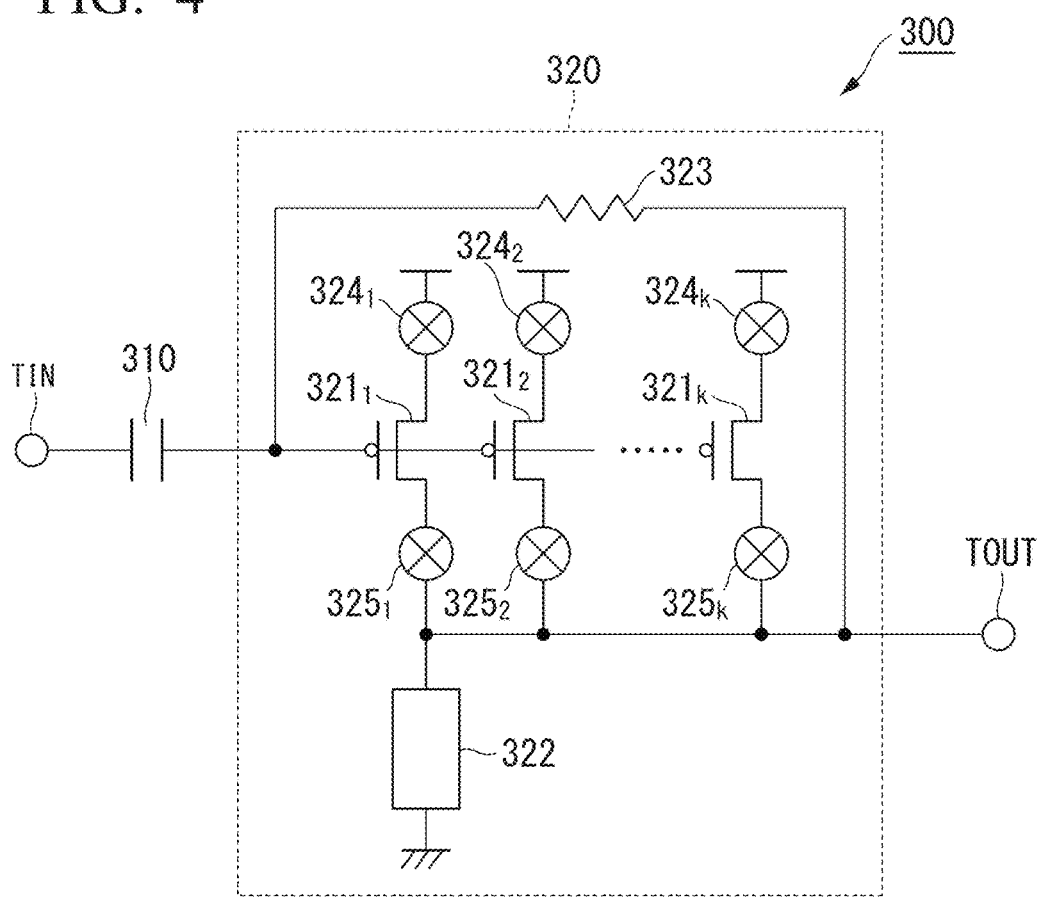
FIG. 4 is a circuit diagram illustrating a configuration example of an amplification unit that is included in the signal detection unit according to the embodiment of the present invention.

FIG. 4 is a circuit diagram illustrating a configuration example of the amplification unit 300. The amplification unit 300 includes a capacitor 310 for intercepting a direct-current component of an input signal that is input through an input terminal TIN, and an amplifier 320 for amplifying an alternating-current component of the input signal. One electrode of the capacitor 310 is connected to the input terminal TIN, and the other electrode is connected to an input part of the amplifier 320.

The amplifier 320 includes a transistor group for adjusting its electrical characteristics (for example, its gain). For example, with post-processing and the like, one or several transistors that constitute the transistor group are selectively connected in parallel to each other in such a manner that desired electrical characteristics are obtained. Specifically, the amplifier 320 includes k pMOS transistors $321_1$ to $321_k$ (k is a natural number equal to greater than 2) that are organic transistors, a load 322, and a resistor 323, and is configured as a so-called single end type amplifier. Among these, the pMOS transistors $321_1$ to $321_k$ constitute the transistor group for adjusting the electrical characteristics of the amplifier 320. Furthermore, with the post-processing and the like, wiring formation regions $324_1$ to $324_k$ and $325_1$ to $325_k$ for selectively connecting one or several transistors of the pMOS transistors $321_1$ to $321_k$ in parallel to each other are provided in the amplifier 320.

According to the present embodiment, as a preliminary step of detecting a signal, characteristics of each of the pMOS transistors $321_1$ to $321_k$ are evaluated. Then, based on a result of the evaluation, the pMOS transistors $321_1$ to $321_k$ are selectively connected in parallel to each other in such a manner as to obtain desired electrical characteristics. For example, if, as a result of the evaluation, the electrical characteristics of the amplifier 320 that result when the pMOS transistor $321_1$ and the pMOS transistor $321_k$ are connected in parallel to each other are closer to target electrical characteristics than characteristics that are obtained by combinations of any other transistors, wiring is formed in the wiring formation regions $324_1$ and $324_k$ and the wiring formation regions $325_1$ and $325_k$, and thus the pMOS transistor $321_1$ and the pMOS transistor $321_k$ are connected in parallel to each other between the power supply node and an output terminal TOUT. In this manner, a suitable combination of multiple pMOS transistors $321_1$ to $321_k$ is selected, and thus dispersion of the electrical characteristics of the amplifier 320 due to characteristics of a pMOS transistor is reduced.

Moreover, the example described above does not impose any limitation. A circuit configuration of the amplification unit 300 is arbitrary. For example, a pseudo CMOS inverter that is disclosed in NPL 1 can be used. According to the following example, an inverter that uses an AC combination load is employed as an amplifier. Such an inverter will be described in detail below.

The local word lines $LWL_1$ to $LWL_{4m}$, the global word lines $GWL_1$ to $GWL_m$, and each output part of the detection signal selection units $GS_1$ to $GS_n$ are connected to an external information processing apparatus (for example, a personal computer) through a suitable interface. However, the example does not impose any limitation. A decoder or a shift register for selecting the local word lines $LWL_1$ to $LWL_{4m}$ and the global word lines $GWL_1$ to $GWL_m$ may be included in the signal detection device 1.

According to the present embodiment, as described below, the electrodes $100_1$ to $100_4$, the electrode signal selection unit 200, and the amplification unit 300 are formed on a flexible substrate. Among these, the electrodes $100_1$ to $100_4$ and the electrode signal selection unit 200 are formed on one surface side of the substrate. The amplification unit 300 is formed in the substrate or on the other surface side of the substrate, along with the detection signal selection units $GS_1$ to $GS_n$ that are illustrated in FIG. 1 to form a multi-layer structure together with the electrodes $100_1$ to $100_4$ and the electrode signal selection unit 200. That is, the amplification unit 300 is made to form the laminated structure together with the electrodes $100_1$ to $100_4$ and the electrode signal selection unit 200, and thus is formed on a layer of the substrate, which is different from a layer on which the electrodes $100_1$ to $100_4$ and the electrode signal selection unit 200 are formed.

Moreover, according to the present embodiment, the electrodes $100_1$ to $100_4$ and the electrode signal selection unit 200 are formed on one surface side of the substrate, and the amplification unit 300 is formed in the substrate or on the other surface side of the substrate. However, if the electrodes $100_1$ to $100_4$ and the electrode signal selection unit 200 form the multi-layer structure, these elements can be arbitrarily arranged in the substrate. Furthermore, the substrate does not necessarily need to have pliability, depending on the purpose.

As described above, the signal detection device 1 according to the present embodiment includes multiple signal detection blocks in which the signal detection units F, each of which is made from the electrodes $100_1$ to $100_4$, the electrode signal selection unit 200, and the amplification unit 300, are arranged, as one signal detection block, in the form of a matrix. In addition, the signal detection device 1 includes the detection signal selection units $GS_1$ to $GS_n$ for selecting a detection signal from each of the signal detection blocks described above. Here, with a block configuration according to the present embodiment, for example, in the electrode signal selection unit 200 that is illustrated in FIG. 3, the load electric current source 220 is shared by the four source follower circuits $210_1$ to $210_4$. This is also the same in the detection signal selection units $GS_1$ to $GS_n$. Therefore, with the block configuration according to the present embodiment, with a signal configuration in terms of a circuit configuration, it is possible to detect the biological signal through multiple electrodes while decreasing the number of signal wiring lines.

Moreover, according to the present embodiment, the signal detection device 1 is configured to include the multiple signal detection blocks described above, but each of the signal detection unit $F_{1,1}$ to $F_{m,n}$ that constitute each of the signal detection blocks may be set to be a single signal detection device. The signal detection device in this case is configured to include the electrode group 100, the electrode signal selection unit 200, the amplification unit 300, and a substrate have pliability, on which these are formed.

Figure 5:
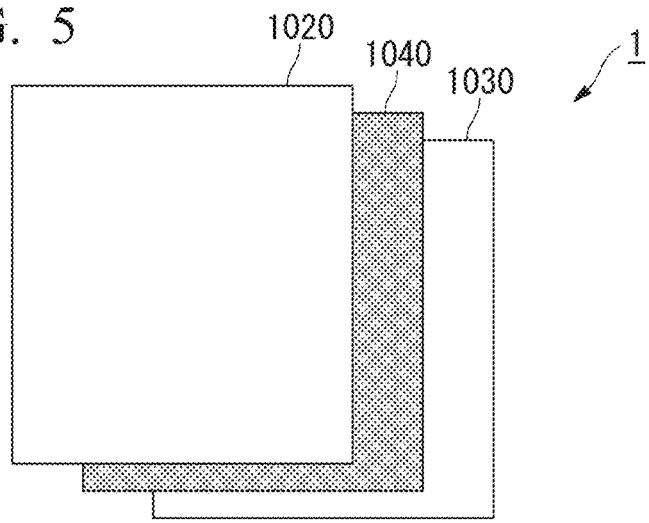
FIG. 5 is a diagram that schematically illustrates a (entire) device structure of the signal detection device according to the embodiment of the present invention.
Figure 6:
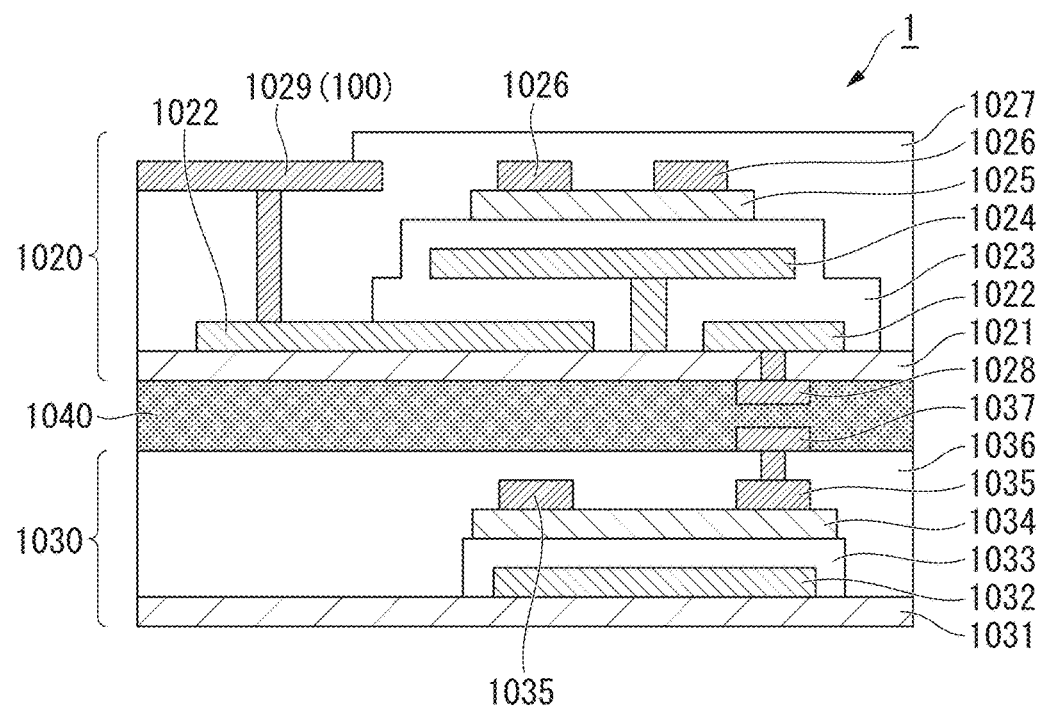
FIG. 6 is a diagram that schematically illustrates a cross-sectional device structure of the signal detection device according to the embodiment of the present invention.

Next, a device structure of the signal detection device 1 is described referring to FIGS. 5 and 6.

FIG. 5 is a diagram that schematically illustrates the (entire) device structure of the signal detection device 1. As illustrated in FIG. 5, mostly, the signal detection device 1 is configured from a first circuit layer 1020, a second circuit layer 1030, and a conductive layer 1040 that is made from an anisotropic conductive sheet, and has a multi-layer structure in which the first circuit layer 1020 and the second circuit layer 1030 are stacked on top of one another in the sheet-like form with a conductive layer 1040 in between. According to the present embodiment, the anisotropic conductive sheet, for example, is made of a material that results for uniformly distributing conductive particles in a highly insulating adhesive agent. Instead of the anisotropic conductive sheet, what is used for electrically connecting electrodes in an electronic product such as a liquid display can be used.

In addition to being in the sheet-like form, the anisotropic conductive sheet may be like a sheet that results from locally stacking an anisotropic conductive sheet on terminal parts necessary for electrical connection between the first circuit layer 1020 and the second circuit layer 1030, in the form of a patch. In this circumstance, in addition to an anisotropic conductive sheet in the form of a patch, an adhesive layer for increasing adhesive strength for stacking the first circuit layer 1020 and the second circuit layer 1030 may be arranged side by side.

Here, the first circuit layer 1020 is a circuit layer that results from arranging multiple electrode groups 100, each of which is made from the electrodes $100_1$ to $100_4$ described above, and multiple electrode signal selection units 200 in the form of a matrix, corresponding to the signal detection units $F_{1,1}$ to $F_{m,n}$. Furthermore, the second circuit layer 1030 is a circuit layer that results from arranging multiple amplification units 300, each of which constitutes each of the signal detection units $F_{1,1}$ to $F_{m,n}$ described above, and multiple detection signal selection units $GS_1$ to $GS_n$ in the form of a matrix, corresponding to the signal detection units $F_{1,1}$ to $F_{m,n}$. According to the present embodiment, the local word lines $LWL_1$ to $LWL_{4m}$ are formed on the first circuit layer 1020, and the global word lines $GWL_1$ to $GWL_m$ are formed on the second circuit layer 1030. However, this example does not impose any limitation, and the local word lines $LWL_1$ to $LWL_{4m}$ and the global word lines $GWL_1$ to $GWL_m$ may be formed on any circuit layer.

FIG. 6 is a diagram that schematically illustrates the (cross-sectional) device structure of the signal detection device 1. As illustrated in FIG. 6, the first circuit layer 1020 and the second circuit layer 1030 are stacked with the conductive layer 1040 made from the anisotropic conductive sheet in between.

Each circuit layer will be specifically described. The first circuit layer 1020 is configured from a polyimide layer 1021 (for example, with a film thickness of 1.2 μm) that is a substrate having flexibility, a metal layer 1022 (for example, Al with a film thickness of 30 nm) that serves as wiring, an AlOx/SAM layer 1023 (for example, AlOx with a film thickness of 4 nm+SAM with a film thickness of 2 nm) that is a gate insulating film of an organic transistor (a pMOS transistor) that constitutes the electrode signal selection unit 200 that is illustrated in FIG. 2, an aluminum layer 1024 (for example, with a film thickness of 30 nm) that is a gate electrode of the organic transistor, an organic semiconductor 1025 (for example, with a film thickness of 30 nm) that is a channel formation layer of the organic transistor, a metal layer (Au) 1026 that is source and drain electrodes of the organic transistor, a parylene layer 1027 (for example, with a film thickness of 2 μm), and metal layers (Au) 1028 and 1029 that are connected to wiring. Here, the metal layer 1029 is an element that is equivalent to the electrodes $100_1$ to $100_4$ which constitute the electrode group 100 that is illustrated in FIG. 2. The metal layer 1028 and the metal layer 1029 are exposed to a lower surface and an upper surface of the first circuit layer 1020, respectively.

As a substrate having flexibility (pliability), which constitutes the first circuit layer 1020, in addition to the polyimide layer, there is a polyethylenenaphthalate (PEN) film, a polyethylene terephthalate (PET) film, a polyether ether ketone (PEEK) film, paraxylylene-based polymer, a composite film that results from stacking an inorganic film such as $SiO_2$ or SiN in order to impart a gas barrier property on these organic films, and the like.

The second circuit layer 1030 is configured from a polyimide layer 1031 (for example, with a film thickness of 1.2 μm) that is a substrate having flexibility, an aluminum layer 1032 (for example, 30 nm) that is a gate electrode of an organic transistor (a pMOS transistor) that constitutes the amplification unit 300 that is illustrated in FIG. 2, an AlOx/SAM layer 1033 (for example, AlOx with a film thickness of 4 nm+SAM with a film thickness of 2 nm) that is a gate insulating film of the organic transistor, an organic semiconductor layer 1034 (for example, a film thickness of 30 nm) that is a channel formation layer of the organic transistor, a metal layer (Au) 1035 that is source and drain electrodes of the organic transistor, a parylene layer 1036 (for example, a film thickness of 2 μm), and a metal layer (Au) 1037 that is connected to the source and drain electrodes of the organic transistor. The metal layer 1037 is exposed to an upper surface of the second circuit layer 1030.

As a substrate having flexibility (pliability), which constitutes the second circuit layer 1030, in addition to the polyimide layer, there are a polyethylenenaphthalate (PEN) film, a polyethylene terephthalate (PET) film, a polyether ether ketone (PEEK) film, paraxylylene-based polymer, a composite film that results from stacking an inorganic film such as $SiO_2$ or SiN in order to give gas barrier property on these organic films, and the like.

When the substrate of the first circuit layer 1020 and the substrate of the second circuit layer 1030 are configured to be made of the same material, this is desirable because thermal distortion can be made uniform an and an occurrence of curvature of a multi-layer substrate that results from the first circuit layer 1020 and the second circuit layer 1030 can be suppressed. Furthermore, it is desirable that each of the substrate of the first circuit layer 1020 and the substrate of the second circuit layer 1030 be thin films having pliability. The thickness of each of the substrates is equal to or less than 75 μm, desirably equal to or less than 25 μm, and more desirably equal to or less than 10 μm but equal to or more than 1 μm.

The first circuit layer 1020 and the second circuit layer 1030 are stacked with the conductive layer 1040 in between. Accordingly, the metal layer 1037 formed on an upper surface of the second circuit layer 1030 and the metal layer 1028 formed on a lower surface of the first circuit layer 1020 are electrically connected to each other. According to the present embodiment, the metal layer 1037 and the metal layer 1028 are electrically connected to each other with the conductive layer 1040 in between, and thus the output part of the electrode signal selection unit 200 and the input part of the amplification unit 300 that are illustrated in FIG. 2 are connected to each other.

Furthermore, in the device structure of the signal detection device 1 that is illustrated in FIG. 6, the second circuit layer 1030 on which the amplification unit 300 and the detection signal selection units $GS_1$ to $GS_n$ are formed is arranged on a lower film side below the first circuit layer 1020 on which the electrode group 100 and the electrode signal selection unit 200 that are described above are formed. Here, with the device structure according to the present embodiment, which is described above, the four electrodes $100_1$ to $100_4$ that are formed on the first circuit layer 1020 are stacked on one amplification unit 300 that is formed on the second circuit layer 1030. For this reason, the size of each and an arrangement pitch between each of the electrodes $100_1$ to $100_4$ can be decreased and the four electrodes can be arranged for one amplification unit. Therefore, an electrode density can be four times that in a technology in NPL 1 described above. Furthermore, because the electrode signal selection unit 200 that is made from the source follower circuits $210_1$ to $210_4$ is formed on the first circuit layer 1020, along with the electrodes $100_1$ to $100_4$, a wiring path over which the biological signals on the electrodes $100_1$ to $100_4$ is input into the electrode signal selection unit 200 can be shortened. For this reason, superimposition of a noise signal onto the biological signal on a signal path can be efficiently suppressed, a and an SN ratio of the detection signal can be improved. Therefore, with the device structure according to the present embodiment, which is described above, it is possible to detect a distribution of the biological signal in a detailed, more stable manner.

Moreover, according to the present embodiment, wiring (not illustrated) for transmitting to the outside the output signals $G_1$ to $G_n$ of the detection signal selection units $GS_1$ to $GS_n$ in FIG. 1, which are formed on the second circuit layer 1030 is pulled out to a lower surface side of the second circuit layer 1030. Furthermore, all control wiring lines that include the local word line LWL and the global word line GWL are pulled out to a lower surface side of the second circuit layer 1030 as well. Accordingly, the wiring lines that are pulled out to the outside from the signal detection device 1 and the subject can be presented from coming into contact with each other.

Description of Operation

Next, operation of the signal detection device 1 according to the present embodiment is described.

The signal detection device 1 is set to detect a surface myoelectric signal (a biological signal) of a human arm. The signal detection device 1 is assumed to be mounted on the human arm in such a manner that the electrodes $100_1$ to $100_4$ that constitutes each of the signal detection units $F_{1,1}$ to $F_{m,n}$ come into contact with a surface of the human arm. Here, for brief description, a case is described where the surface myoelectric signal is detected through the electrode $100_1$ that constitutes the signal detection unit $F_{1,1}$. In this case, a signal level of each selection signal on the global word lines $GWL_1$ to $GWL_m$ is set in such a manner that the detection signal selection units $GS_1$ to $GS_n$ select the detection signals $S_{1,1}$ to $S_{1,n}$ of the signal detection units $F_{1,1}$ to $F_{1,n}$ in the first row, respectively. Specifically, a signal level of the global word line $GWL_1$ is set to a logical level "0", and each signal level of the other global word lines $GWL_2$ to $GWL_m$ is set to a logical level "1". Furthermore, a signal level of each selection signal on the local word lines $LWL_1$ to $LWL_4$ is set in such a manner that the electrode signal selection unit 200 which constitutes each of the signal detection units $F_{1,1}$ to $F_{1,n}$ in the first row selects only a signal that is input through the electrode $100_1$. Specifically, a signal level of the local word line $LWL_1$ is set to the logical level "0" and each signal level of the local word lines $LWL_2$, $LWL_3$, and $LWL_4$ is set to the logical level "1".

Moreover, according to the present embodiment, each signal level of the local word lines $LWL_5$ to $LWL_{4m}$ is assumed to be set in such a manner that the surface myoelectric signal which is input through the electrodes $100_1$ to $100_4$ that constitute each of the signal detection units in second to m-th rows is in a non-selection state. However, this example does not impose any limitation. The signal detection units in the second to m-th rows may function in the same manner as the signal detection units in the first row, but the detection signals that are finally output as the output signals $G_1$ to $G_n$ from the detection signal selection units $GS_1$ to $GS_n$, respectively, are detection signals for one row, which are selected by the detection signal selection units $GS_1$ to $GS_n$, respectively.

As described above, when the signal level of each selection signal on the local word lines $LWL_1$ to $LWL_{4m}$ and the global word lines $GWL_1$ to $GWL_m$ is set, the surface myoelectric signals that originate from arm muscles are input, as the electrode signals, into the electrode signal selection unit 200, through the electrodes $100_1$ to $100_4$ that constitute the signal detection unit $F_{1,1}$. Based on each signal level of the local word lines $LWL_1$ to $LWL_4$, the electrode signal selection unit 200 selects the surface myoelectric signal that is input as an electrode signal through the electrode $100_1$, and outputs the selected surface myoelectric signal as an electrode signal S200.

Specifically, as described, because the signal level of the local word line $LWL_1$ is set to "0", the pMOS transistor 211 that constitutes the source follower circuit $210_1$ is controlled in such a manner that the pMOS transistor 211 is in an ON state. Accordingly, the source of the pMOS transistor 212 is electrically connected to the node N200 through the pMOS transistor 211.

On the other hand, the surface myoelectric signal that is input as the electrode signal through the electrode $100_1$ is applied to the gate of the pMOS transistor 212 of the source follower circuit $210_1$. A source voltage of the pMOS transistor 212 is driven by the pMOS transistor 221 of the load electric current source 220 through the pMOS transistor 211, to a voltage that is higher by a gate threshold voltage VT of the pMOS transistor 212 than a gate potential of the pMOS transistor 212. In other words, the source voltage of the pMOS transistor 212 (=a source voltage of the pMOS transistor 211) that is driven by the pMOS transistor 221 of the load electric current source 220 is clamped to the voltage that is higher by the gate threshold voltage VT of the pMOS transistor 212 than the gate potential of the pMOS transistor 212. Accordingly, the source follower circuit $210_1$ outputs a voltage signal according to the surface myoelectric signal that is input through the electrode $100_1$, as the electrode signal S200 through the node N200. Finally, the electrode signal selection unit 200 selects an electrode signal that is input through the electrode $100_1$, from among the surface myoelectric signals that are input as electrode signals through the electrodes $100_1$ to $100_4$, respectively, and outputs the selected electrode signal as the electrode signal S200.

The electrode signal S200 that is output from the source follower circuit $210_1$ is supplied, as an output signal of the electrode signal selection unit 200, to the input part of the amplification unit 300. The amplification unit 300 amplifies the electrode signal S200 that is supplied from the electrode signal selection unit 200 and outputs the detection signal $S_{1,1}$. The detection signal $S_{1,1}$ that is output from the amplification unit 300 is supplied, as an output signal of the signal detection unit $F_{1,1}$ to the detection signal selection unit $GS_1$. Based on the same operating principle as with the electrode signal selection unit 200, the detection signal selection unit $GS_1$ selects the detection signal $S_{1,1}$ that is supplied from the signal detection unit $F_{1,1}$ and outputs the selected detection signal $S_{1,1}$ as the output signal $G_1$. In the same manner, the output signals $G_2$ to $G_n$ are output from the other detection signal selection units $GS_2$ to $GS_n$, respectively.

The output signals $G_1$ to $G_n$ of the biological signal selection units $GS_1$ to $GS_n$ are input into an external information processing device that is not illustrated. The external information processing device implements predetermined signal processing on the signal that is input, and thus generates a strength distribution of the detection signal from each signal detection unit. For example, the external information processing device samples the detection signal from each signal detection unit and converts the sampled detection signal into a digital signal. Then the external information processing device generates the strength distribution (a two-dimensional distribution of signal strength) of the detection signal from each of the signal detection units $F_{1,1}$ to $F_{1,n}$ in the first row, and displays the generated strength distribution on a display unit (not illustrated). In the same manner, scanning is implemented on the signal detection units in a different row, and the strength distribution of the detection signal from each of the signal detection units $F_{1,1}$ to $F_{m,n}$ is obtained. An operator can specify a portion at which the signal strength indicating an abnormality occurs, from the strength distribution obtained by the scanning described above. However, this example does not impose any limitation, and a form of display of the signal strength is arbitrary.

With a circuit configuration of the signal detection device 1 according to the present embodiment, which is described, in the signal detection unit $F_{1,1}$, an amplitude of a voltage signal that is output as the electrode signal S200 from the source follower circuit $210_1$ remains approximately the same amplitude as that of an input signal of the source follower circuit $210_1$, that is, the surface myoelectric signal (the biological signal) that is applied to the gate of the pMOS transistor 212 through the electrode $100_1$. However, because output impedance of the source follower circuit $210_1$ is sufficiently smaller than impedance of the living body (the human arm) that generates the surface myoelectric signal, the electrode signal S200 that is input from the source follower circuit $210_1$ into the amplification unit 300 is subject to hardly any influence of ambient noise. Furthermore, because the detection signal selection unit $GS_1$ that selects the electrode signal S200 that is output from the signal detection unit $F_{1,1}$ as well as the electrode signal selection unit 200, is configured from the source follower circuit, the output signal $G_1$ of the detection signal selection unit $GS_1$ is subject to hardly any ambient noise. Therefore, according to the present embodiment, an SN ratio of the detection signal can be effectively improved, and it is possible to detect the biological signal with high precision. Furthermore, as described above, according to the present embodiment, because the multiple signal detection blocks are included in which the signal detection units F, each of which is made from the electrodes $100_1$ to $100_4$, the electrode signal selection unit 200, and the amplification unit 300 are arranged, as one signal detection block, in the form of a matrix, the number of signal wiring lines can be reduced. For this reason, an influence of crosstalk between the wiring lines and the like can be suppressed, and it is possible to detect the biological signal with much higher precision.

Furthermore, with the device structure of the signal detection device 1 according to the present embodiment, which is described above, the electrode density can be increased, and the signal path from each of the electrodes $100_1$ to $100_4$ to the amplification unit 300 can be controlled to be shortened. Accordingly, the influence of the noise on the signal path can be suppressed, and it is possible to furthermore improve the SN ratio of the detection signal, along with an effect of improving the SN ratio, which results from the circuit configuration described above. Therefore, according to the present embodiment, although the electrodes are arranged at a high density, a noise component due to the crosstalk and the like can be suppressed, and the strength distribution of the biological signal can be measured with high precision.

Furthermore, according to the present embodiment, because the multiple signal detection units $F_{1,1}$ to $F_{m,n}$ can be arbitrarily selected, and multiple electrodes that constitute each signal detection unit can be arbitrarily selected, when the signal detection device 1 is mounted on the subject, there is no need to strictly specify a portion that has to be monitored, in advance. Therefore, the mounting of the signal detection device 1 on the subject can be made easy. Furthermore, the biomedical signal of an arbitrary portion within a range where the signal detection units $F_{1,1}$ to $F_{m,n}$ are positioned can be selectively detected, without being limited to an abnormal portion.

The signal detection device according to the embodiment of the present invention is described above as being realized, but the present invention can be realized as a signal detection method. In this case, the signal detection method according to the present invention can be realized as a signal detection method that includes a selection step of causing an electrode signal selection unit 200 to select one electrode from among signals on multiple electrodes $100_1$ to $100_4$ that are arranged to come into contact with a subject that generates a biological signal, based on a selection signal, and an amplification step of causing an amplification unit 300 to amplify a signal that is selected by the electrode signal selection unit 200 in the selection step, in which the multiple electrodes $100_1$ to $100_4$, the electrode signal selection unit 200, and the amplification unit 300 are formed on a substrate having pliability, the multiple electrodes and the electrode signal selection unit are formed on the substrate, and the amplification unit is formed on the substrate to form a multi-layer structure together with the multiple electrodes and the electrode signal selection unit.

Furthermore, the present invention can be realized as a method of manufacturing the signal detection device described above. The method of manufacturing the signal detection device in this case is a method of manufacturing a signal detection device that includes multiple electrodes $100_1$ to $100_4$ that are arranged to come into contact with a subject that generates a biological signal, an electrode signal selection unit 200 that alternatively selects one signal from signals on the multiple electrodes, based on a selection signal, an amplification unit 300 that amplifies the signal that is selected by the electrode signal selection unit 200, and a substrate having pliability, on which the multiple electrodes $100_1$ to $100_4$, the electrode signal selection unit 200, and the amplification unit 300 are formed, the method including a step of forming the multiple electrodes and the electrode signal selection unit on the substrate and a step of forming the amplification unit on the substrate to form a multi-layer structure together with the multiple electrodes and the electrode signal selection unit.

The embodiment of the present invention is described above, but the present invention is not limited to the embodiment described above. Various amendments are possible within the scope that does not depart from the gist of the present invention.

For example, according to the embodiment, one electrode is described as being selected by the local word line LWL and the global word line GWL in each column, but for example, multiple electrodes may be selected in units of rows, and multiple electrodes may be selected in units of columns. As long as an electrode is selected based on each signal level of the local word line LWL and the local word line GWL, a combination of electrodes that are selected is arbitrary.

EXAMPLE

An example of the present invention will furthermore be specifically described, but the present invention is not limited to the following example.

Next, the example of the present invention is described referring to FIGS. 7 to 13.

For the purpose of controlling an artificial arm, the inventors developed a 64 channel surface electromyogram (EMG) measurement sheet that has organic transistors (2 V organic transistors) of which a drive voltage is 2 V and that is formed on a PEN film having pliability, as one example of the signal detection device 1 according to the embodiment, which is described above. Amplification in a measurement position of a myoelectric signal in a state where an EMG electrode density increases four times is possible with a distributed sharing amplifier (DSA) architecture. Transistor mismatching is reduced as much as 92% and transistor power is reduced as much as 56%, using a selection and connection (SAC) technique that results from the the post-processing.

Because a surface electromyogram (EMG), which is in the waveform of voltage that occurs on the skin due to the thin muscles, results from noninvasive measurement, the surface electromyogram is important for the purpose of detecting an intention of a human movement as expressed by an artificial arm and an artificial leg. For the purpose of the use in the artificial arm, EMG multi-point measurement is necessary for controlling a hand with precision [References 1 and 2]. However, there are two problems with multi-point measurement in the related art, which uses a passive electrode array [References 1 and 3]. (1) The first problem is that prolonged measurement causes inconvenience to a measured person because EMG electrodes that are attached to a skin surface lack pliability. (2) The second problem is that because as the number of measurement points increases, the number of wiring lines increases between each of the electrodes and the upstream circuit, EMG reception quality is degraded. In order to overcome these problems, a surface EMG measurement sheet (SEMS) for controlling the artificial hand was developed. The surface EMG measurement sheet results from integrating an EMG electrode array and an upstream amplifier array that includes a 2 V organic transistor on a film with a thickness of 1 μm, which has super-pliability. With the developed SEMS, it is possible to perform the measurement with a lower burden over a long time without degrading reception quality.

Problems with a design of an organic transistor for an amplifier array are (1) that a large area of an amplifier increases a pitch of an electrode array, and (2) that mismatching of an amplifier is due to an large amount of mismatching of the organic transistor. In order to overcome these problems, the present specification discloses two proposals. That is, the present specification discloses (1) the distributed sharing amplification (DSA) architecture for amplifying the myoelectric signal to a density four times the EMG electrode density, and (2) the selection and connection (SAC) technique that results from subsequent manufacturing that reduces mismatching of the transistor that constitutes the amplifier as much as 92% and power consumption as much as 56%, when compared with in-parallel transistors in the related art. DSA and SAC are fundamental technologies for large-scale array measurement of the biological signal that uses a printed electrode that is pliable.

Figure 7:
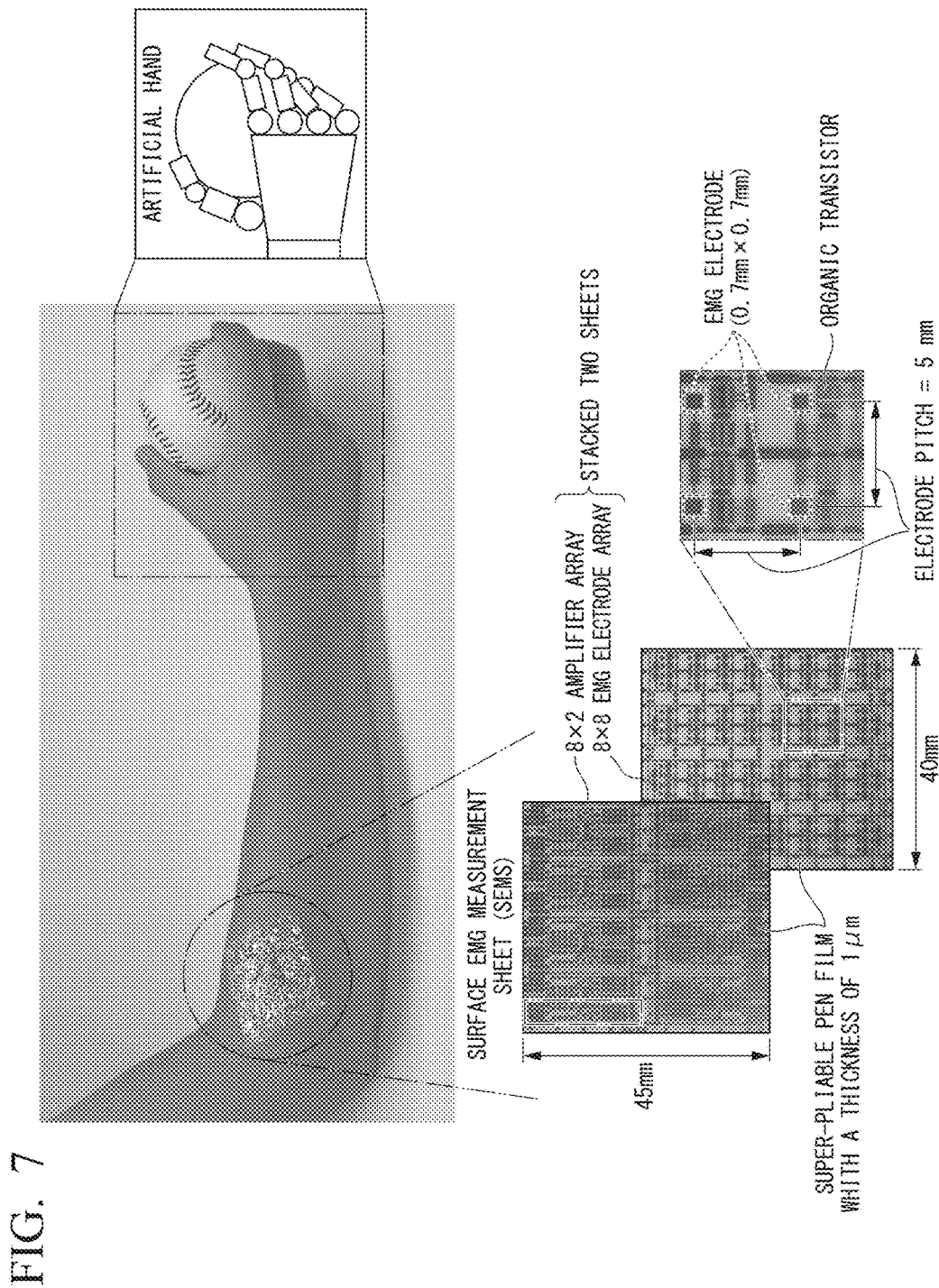
FIG. 7 is a diagram illustrating a picture of a 45 mm×40 mm 64 channel SEMS according to an example of the present invention.

FIG. 7 is a picture of a 45 mm×40 mm 64 channel SEMS that has been developed by the inventors. In the SEMS, an 8×8 EMG electrode array sheet and an upstream 8×2 amplifier array sheet having a 2 V organic transistor are stacked on a polyethylenenaphthalate (PEN) film with a thickness of 1 μm that has super-pliability. A pitch between the EMG electrodes is 0.7 mm, and an area of the 8×8 EMG electrode array is 3.5 m².

Figure 8:
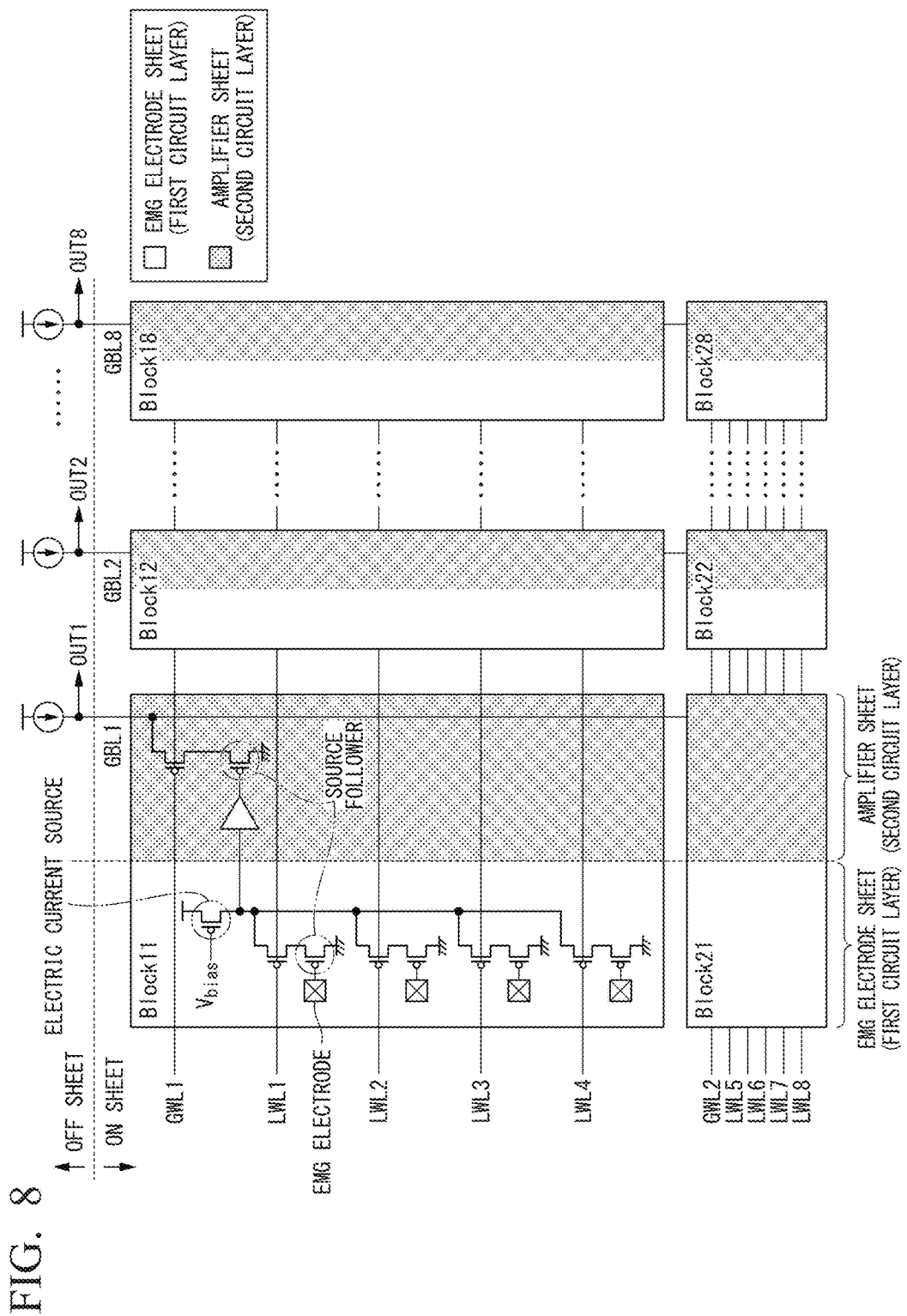
FIG. 8 is a circuit diagram of the SEMS that uses a DSA architecture according to the example of the present invention.
Figure 13:
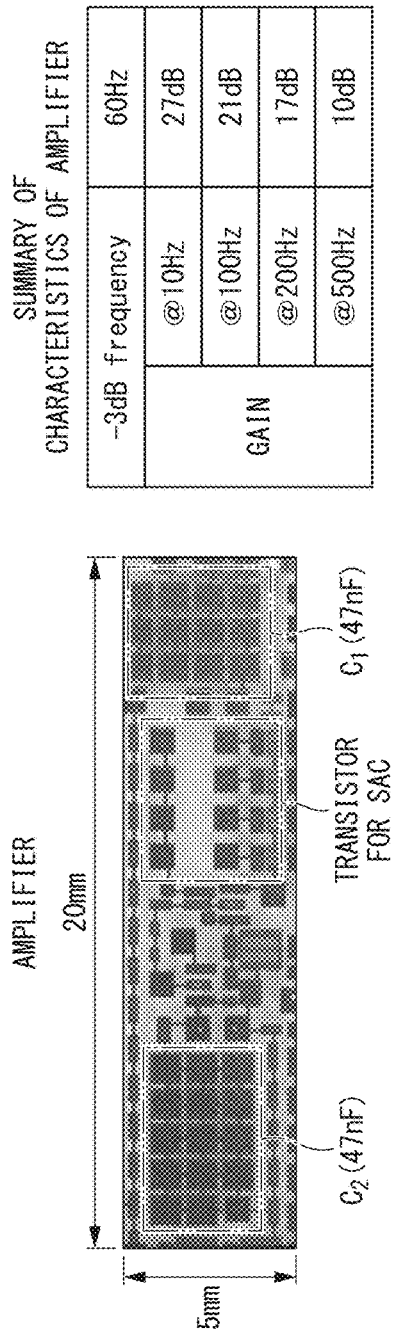
FIG. 13 is a diagram illustrating a picture of the organic amplifier according to the embodiment of the present invention.

FIG. 8 is a circuit diagram of an SEMS that uses the DSA architecture that is disclosed in the present specification. The SEMS includes the amplifier array instead of the passive electrode array [References 1 to 3] in the related art in order to avoid degradation in the signal quality. As illustrated in FIGS. 7 and 13, because an area of the amplifier is large, one amplifier is shared among four electrodes, and this increases the electrode density four times. Furthermore, the EMD electrode array and the amplifier array are formed on an individual sheet that is multi-layered [Reference 4] in order to increase the electrode density. As illustrated in FIG. 8, in a block 11, one electrode is selected by signals in the local word lines ($LWL_1$ to $LWL_4$) from among four EMG electrodes, and a signal due to the source follower is amplified by the amplifier. In a block 21, one electrode is selected by signals in the local word lines ($LWL_5$ to $LWL_8$) from among four EMG electrodes, and a signal due to the source follower is amplified by the amplifier. Then, outputs of these two amplifiers are selected by signals in the local word lines ($GWL_1$ to $GWL_2$). The authors employ a 2 V organic pMOS transistor that uses DNTT organic semiconductor [Reference 5] and a cell array mono layer (SAM) technology [Reference 6], and thus realizes a circuit design using only a pMOS.

Figure 9:
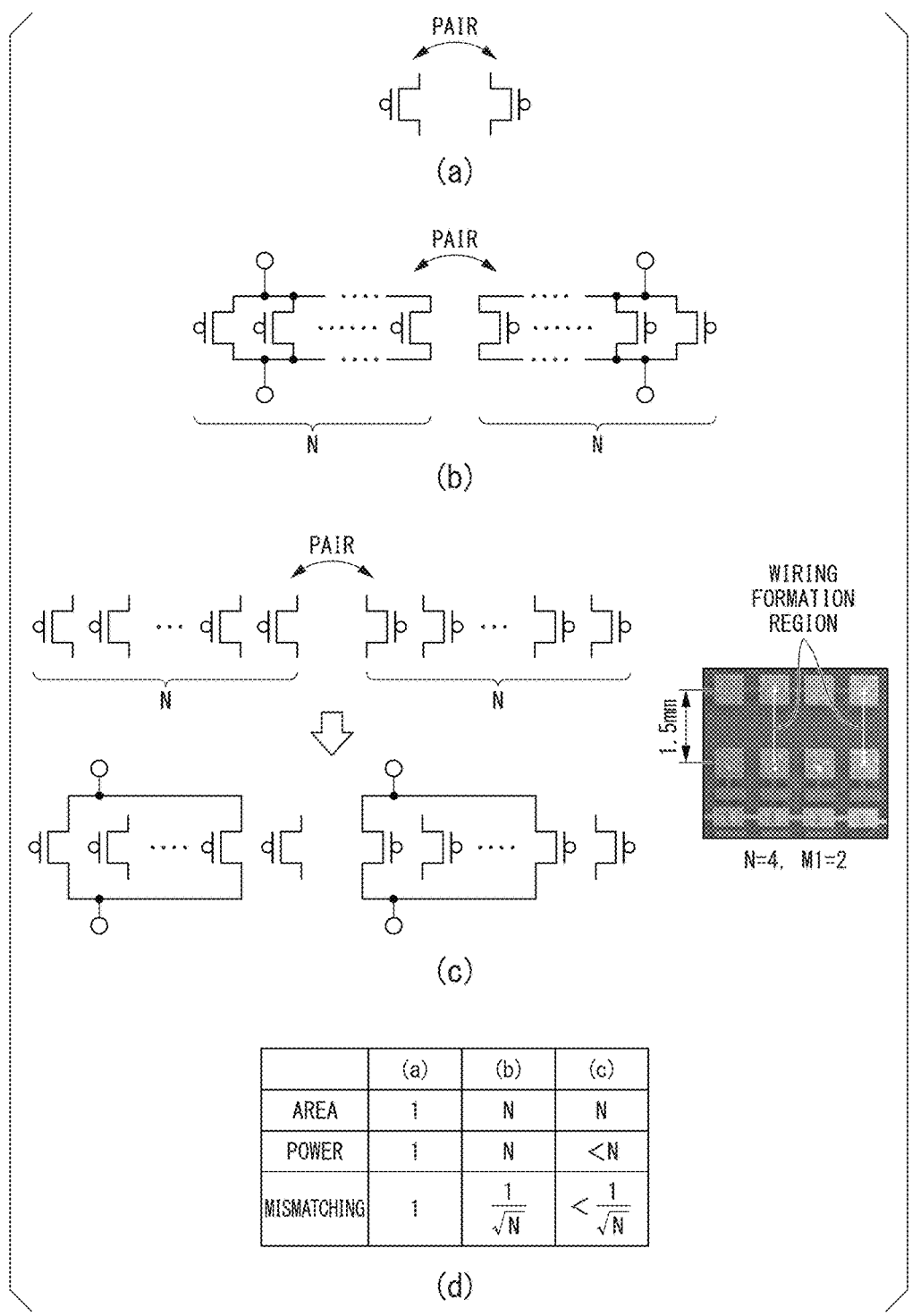
FIG. 9 is a diagram for describing a configuration of a transistor mismatching reduction technology for an amplifier array according to the example of the present invention.

FIG. 9 illustrates a transistor mismatching reduction technology in the related art for the amplifier array and a transistor mismatching reduction technology disclosed in the present specification. FIGS. 9(a) and 9(b) illustrate transistor mismatching between a single transistor and N in-parallel transistors in the related art, respectively.

Figure 10:
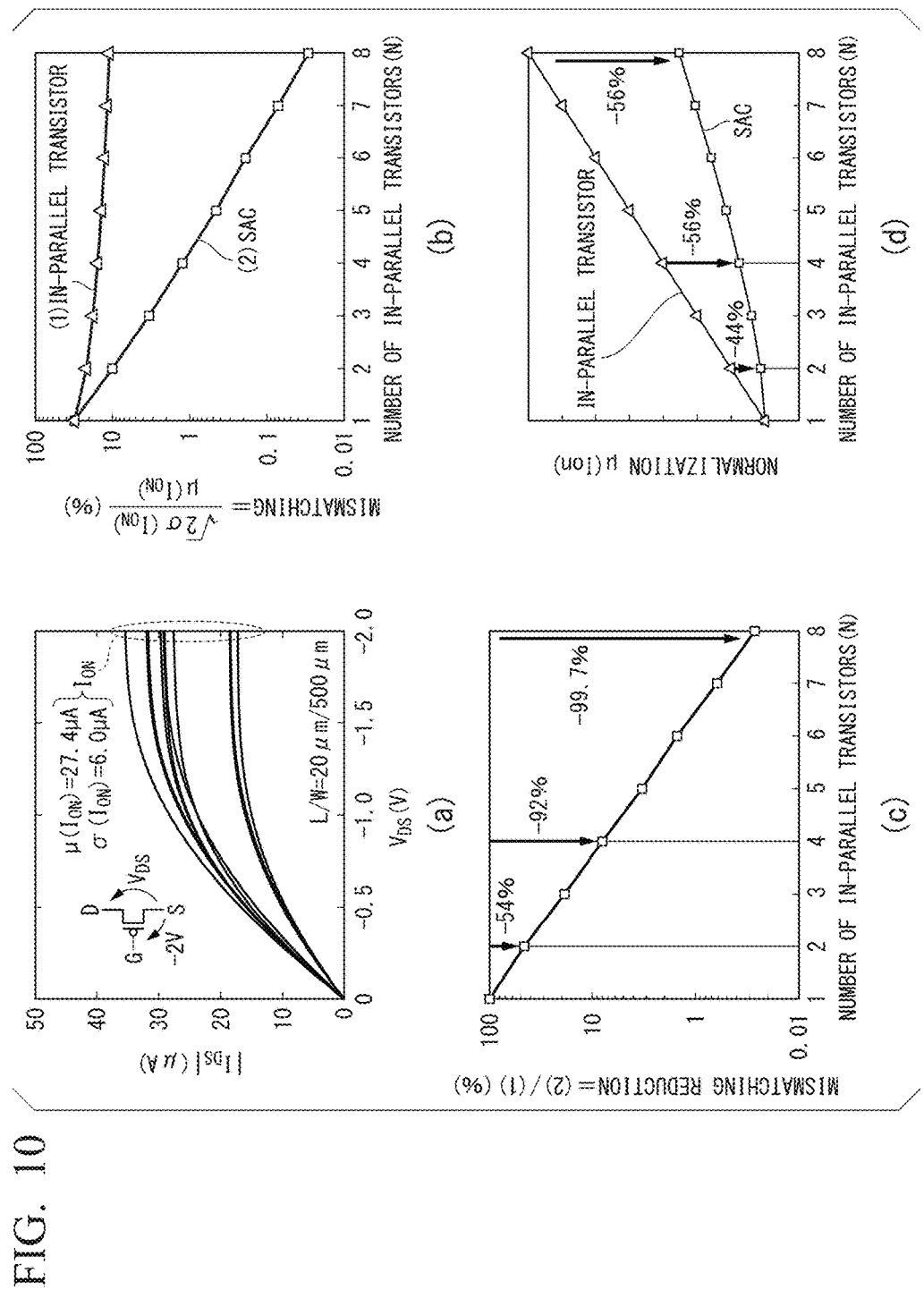
FIG. 10 is a diagram for describing an effect of the transistor mismatching reduction technology for the amplifier array according to the example of the present invention.

FIG. 9(c) illustrates a SAC technique that results from the subsequent manufacturing that is disclosed in the present specification. In the SAC, first, I-V characteristics (for example, a threshold voltage and an Ion current (ion)) of each transistor are measured. The measurement needs to be performed 2N times. Then, based on calculation that reduces the mismatching in a target, $M_1$ transistors and $M_2$ transistors are selected from a left group and a right group of FIG. 9(c), respectively. Normally, $M_1$ and $M_2$ are not equal to each other. Last, as illustrated in a picture in FIG. 9(c), the selected $M_1$ ($M_2$) transistors are connected to each other, using an ink jet printer. While the SAC disclosed in the present specification uses print electronics, the SAC that results from silicon VLSI technology has high costs and is not practical. A comparison table is illustrated in FIG. 9(d). According to the Pelgrom rule, even at the expense of an N-times power increase, the mismatching of N in-parallel transistors (FIG. 9(b)) remains $N^{-1/2}$ times. In contrast, with the SAC (FIG. 9(c)) that is disclosed in the present specification, the transistor mismatching occurs less than $N^{-1/2}$ times, and the power consumed is less than N times. A detailed analysis is illustrated in FIG. 10.

FIG. 10(a) illustrates a result of measuring $I_{DS}$-$V_{DS}$ characteristics of 11 organic pMOS transistors. In the present specification, Ion mismatching is a reduction target. An average (μ(Ion)) of and a sigma (σ(Ion)) of an Ion measurement value are 27.4 μA and 6.0 μA, respectively. Based on μ(Ion) and σ(Ion) that are obtained by the measurement, the Ion mismatching is simulated on an assumption of a normal distribution, and a comparison between the in-parallel transistors (FIG. 9(b)) in the related art and the SAC (FIG. 9(c)) that is disclosed in the present specification is made. FIG.

10(b) illustrates N dependence of the Ion mismatching that is obtained by the simulation. The Ion mismatching of the in-parallel transistors is in proportion to $N^{-1/2}$ according to the Pelgrom rule. On the other hand, the Ion mismatching of the SAC that is disclosed in the present specification occurs sufficiently less often than in the in-parallel transistors in the related art. FIG. 10(c) illustrates the N dependency of the Ion mismatching reduction that is derived by the simulation from FIG. 10(b). For example, if N=2, 4, 8, the Ion mismatching reductions are −54%, −92%, and −99.7%, respectively. N=4 corresponds to an example that is illustrated in FIG. 9(c). FIG. 10(d) illustrates the N dependency (=averaged power) of μ(Ion) that is obtained by the simulation. For example, if N=2, 4, 8, the reductions of μ(Ion) are −44%, −56%, and −56%, respectively. In this manner, with the SAC that is disclosed in the present specification, the mismatching can occur sufficiently less often than in the in-parallel transistors with less power overhead.

Figure 11:
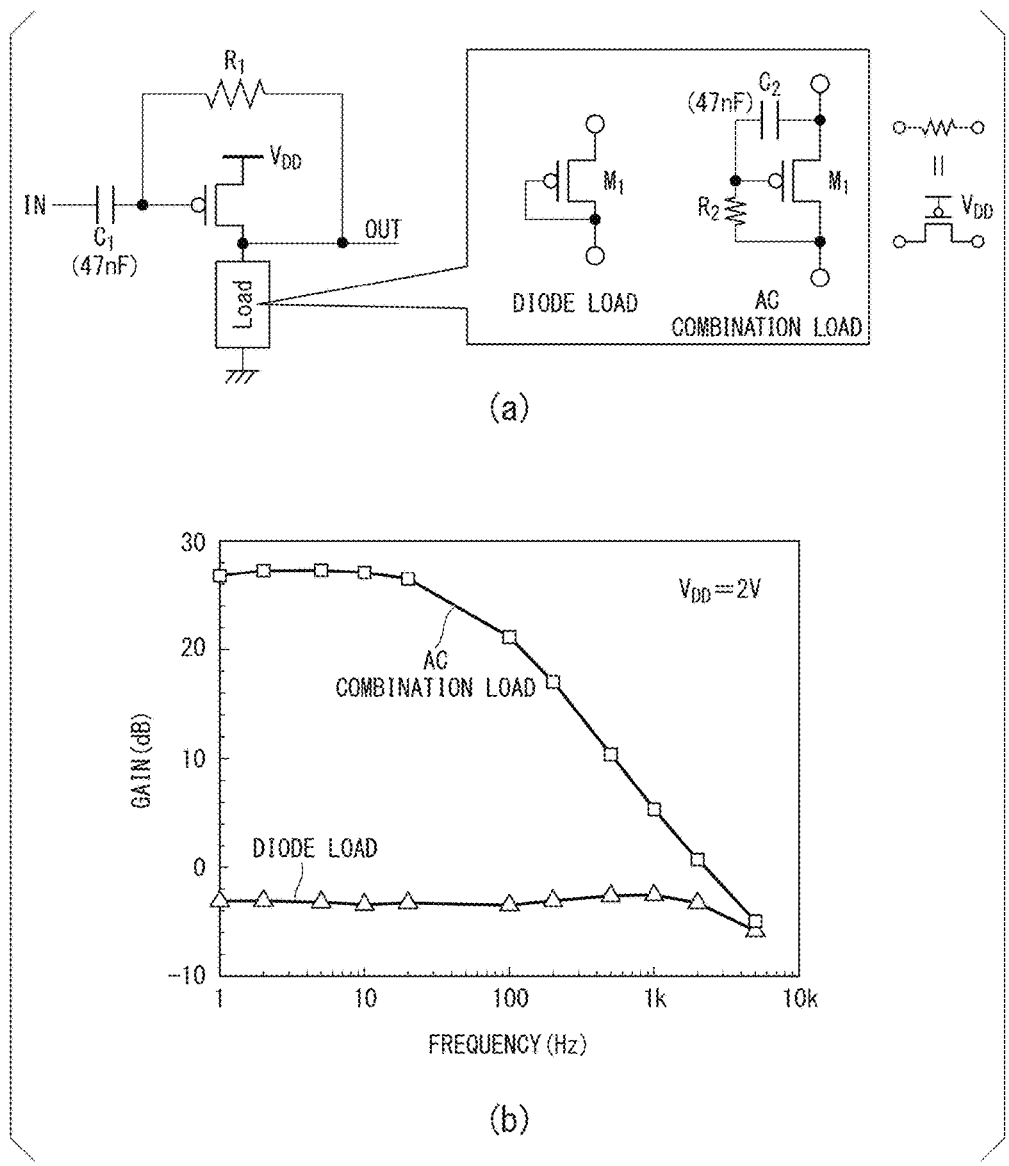
FIG. 11 is a circuit diagram of an amplifier that is made up of only a pMOS that is used in the SEMS according to the example of the present invention.

It is difficult to increase a gain of an amplifier in the circuit design that uses only a pMOS transistor. Although a high gain can be obtained with a pseudo CMOS inverter [References 4 and 7], a negative voltage is needed. Therefore, in the present specification, an amplifier that is only a pMOS transistor having a load that is AC-combined based on [Reference 8] is used and thus the negative voltage is not needed. FIG. 11(a) illustrates a circuit diagram of the amplifier that is only a pMOS transistor that is used in the SEMS. For comparison, a diode load in the related art is also illustrated. In the AC combination load, $V_{GS}$ of a transistor $M_1$ remains constant due to a capacitor $C_2$, and impedance of the load becomes high. Accordingly, a high gain is achieved. Capacitors $C_1$ and $C_2$ are realized by MIM capacitors, and $R_1$ and $R_2$ are realized by pMOS transistors. A size of an amplifier is 20 mm×5 mm, and a picture thereof is illustrated in FIG. 13. FIG. 11 (b) illustrates a result of measuring frequency dependence of a gain of an amplifier at 2 V. A gain of an amplifier that has an AC combination load is sufficiently higher than a gain of an amplifier that has a diode load. Power consumption by the amplifier that has the AC combination load is 30 μW. Target specifications of the amplifier are "gain @100 Hz>20 dB," and "gain @500 Hz>10 dB." That is, the fact is obtained that in the amplifier that has the AC combination load, a gain in a case where a frequency of a voltage that is input is 100 Hz is greater than 20 dB and a gain in a case where the frequency of the voltage that is input is 500 Hz is greater than 10 dB. The reason for this is because for the target specifications described above, a typical amplitude band and a frequency band are 1 mV to 2 mV and 10 Hz to 500 Hz, respectively. In FIG. 11 (b), "gain @100 Hz=21 dB" and "gain @500 Hz=10 dB," are obtained. That is, an effect is obtained in which a gain in a case where the frequency of the voltage that is input is 100 Hz is 21 dB and a gain in a case where the frequency of the voltage that is input is 500 Hz is 10 dB. This satisfies the target specifications described above.

Figure 12:
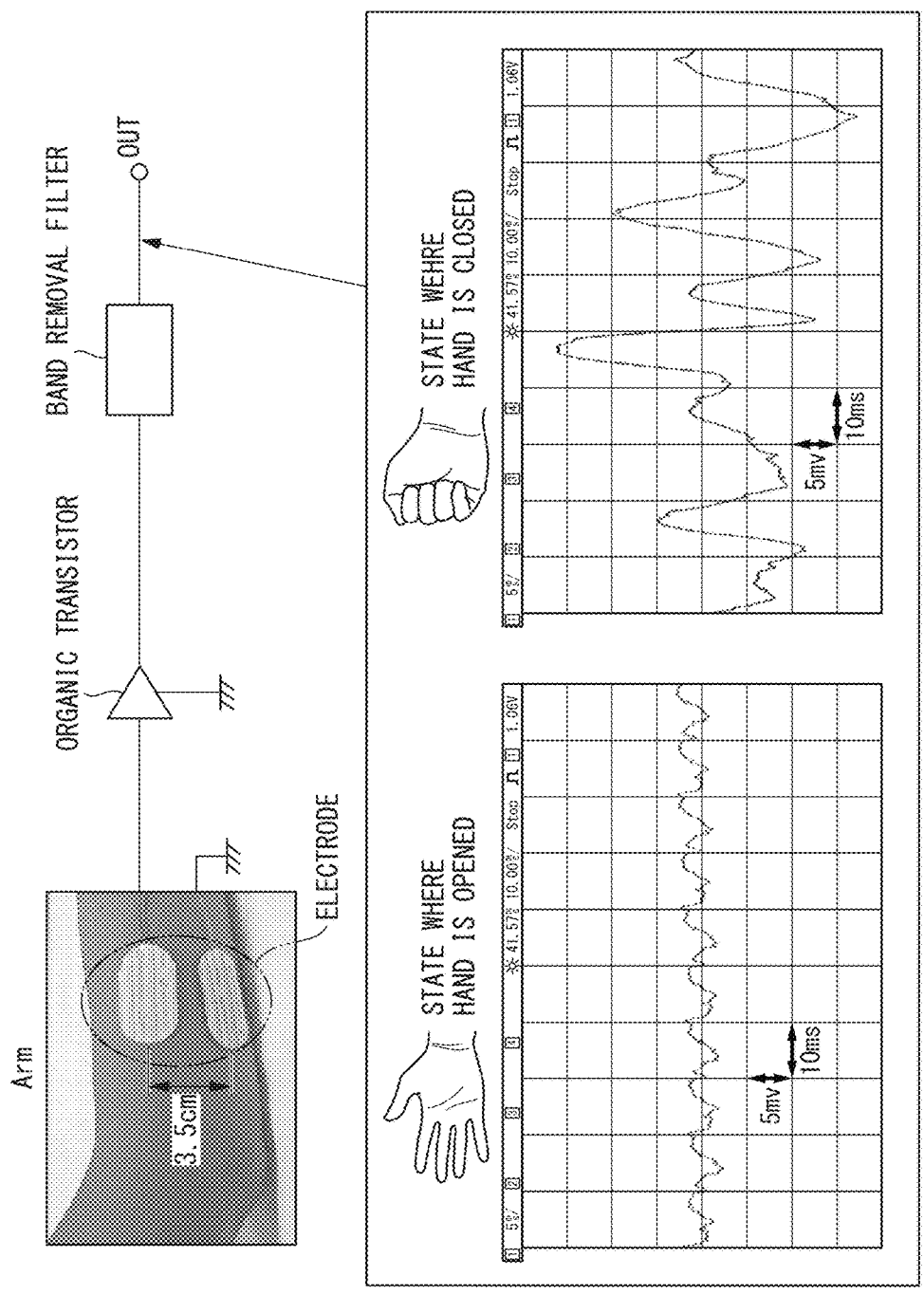
FIG. 12 is a diagram illustrating setting of a measurement system of a surface EMG that has an organic amplifier according to the example of the present invention and a measurement waveform.

FIG. 12 illustrates setting of a measurement system of a surface EMG that has an organic amplifier and a measurement waveform. A distinct difference between a waveform in a state where a hand is opened and a waveform in a state where the hand is closed is satisfactorily observed. A maximum amplitude band of the waveform and a frequency in a state where the hand is opened are 35 mV and 100 Hz, respectively.

FIG. 13 illustrates a picture of the organic amplifier and main characteristics that are put together.

References: [1] P. Liu, et al., "EMG-to-Force Modeling for Multiple Fingers," IEEE AnnualNortheast Bioengineering Conference (NEBEC), pp. 1-2, April 2011. [2] D. Staudenmann, et al., "Towards Optimal Multi-Channel EMG Electrode Configurations in Muscle Force Estimation: A High Density EMG Study," Elsevier Journal of Electromyography and Kinesiology, vol. 15, issue 1, pp. 1-11, February 2005. [3] B. G. Lapatki, et al., "A Thin, Flexible Multielectrode Grid for High-Density Surface EMG," American Physiological Society Journal of Applied Physiology, vol. 96, no. 1, pp. 327-336, January 2004. [4] T. Yokota, et al., "Sheet-Type Organic Active Matrix Amplifier System Using Vth-Tunable, Pseudo-CMOS Circuits with Floating-Gate Structure," IEEE International Electron Devices Meeting, pp. 335-338, December 2011. [5] T. Yamamoto and K. Takimiya, "Facile Synthesis of Highly π-Extended Heteroarenes, Dinaphtho[2,3-b:2',3'-f]chalcogenopheno[3,2-b]chalcogenophenes, and Their Application to Field-Effect Transistors," Journal of American Chemical Society, vol. 129, no. 8, pp. 2224-2225, August 2007. [6] H. Klauk, et al., "Ultralow-Power Organic Complementary Circuits," Nature, vol. 445, pp. 745-748, February, 2007. [7] K. Ishida, et al., "100-V AC Power Meter System-on-a-Film (SoF) Integrating 20-V Organic CMOS Digital and Analog Circuits with Floating Gate for Process Variation Compensation and 100-V Organic PMOS Rectifier," IEEE ISSCC Dig. of Tech. Papers, pp. 218-219, February 2011. [8] H. Marien, et al., "A Fully Integrated ΔΣ ADC in Organic Thin-Film Transistor Technology on Flexible Plastic Foil," IEEE J. Solid-State Circuits, vol. 44, no. 1, pp. 276-284, January 2011.

INDUSTRIAL APPLICABILITY

The present invention can be widely applied to a device for detecting a biological signal. Furthermore, the present invention can be applied to a device for detecting an electrical signal such as that of a manufactured product.

REFERENCE SIGNS LIST

1 SIGNAL DETECTION DEVICE
F, $F_{1,1}$ TO $F_{m,n}$ SIGNAL DETECTION UNIT
G, $GS_1$ TO $GS_n$ BIOLOGICAL SIGNAL SELECTION UNIT
GWL, $GWL_1$ to $GWL_m$ GLOBAL WORD LINE
LWL, $LWL_1$ TO $LWL_{4m}$ LOCAL WORD LINE
100 ELECTRODE GROUP
$100_1$ TO $100_4$ ELECTRODE
200 ELECTRODES SIGNAL SELECTION UNIT
$210_1$ TO $210_4$ SOURCE FOLLOWER CIRCUIT
220 LOAD ELECTRIC CURRENT SOURCE
211, 212, 221 pMOS TRANSISTOR (ORGANIC TRANSISTOR)
300 AMPLIFICATION UNIT
310 CONDENSOR
320 AMPLIFIER
$321_1$ TO $321_k$ pMOS TRANSISTOR (ORGANIC TRANSISTOR)
322 LOAD
323 RESISTOR
$324_1$ to $324_k$, $325_1$ to $325_k$ WIRING FORMATION REGION
1020 FIRST CIRCUIT LAYER
1030 SECOND CIRCUIT LAYER
1040 CONDUCTIVE LAYER

The invention claimed is:

1. A signal detection device comprising:
a first circuit layer having flexibility, in which multiple electrode groups, each of which is made from multiple electrodes configured to come into contact with a subject that generates a signal, and multiple first selection units, each of which selects signals on the multiple electrodes based on a selection signal, are arranged in the form of a matrix;
a second circuit layer having flexibility, in which multiple amplification units, each of which amplifies the signal selected by a first selection unit selected from the multiple first selection units, are arranged in the form of a matrix, and in which a second selection unit that selects a single detection signal which is output from each of the multiple amplification units that are arranged in the form of a matrix is arranged; and
a conductive layer having a sheet shape that is provided between the first circuit layer and the second circuit layer, and that electrically connects an output part of the first selection unit that is formed on the first circuit layer and an input part of an amplification unit selected from the multiple amplification units that are formed on the second circuit layer, wherein
the first circuit layer and the second circuit layer are stacked with the conductive layer in between in such a manner that the amplification unit forms a laminated structure together with an electrode group that is made from the multiple electrodes and the first selection unit, and
the conductive layer is in the form of a sheet having anisotropic conductivity.

2. The signal detection device according to claim 1,
wherein each first selection unit is configured from multiple source follower circuits and each of the multiple source follower circuits includes each of the multiple electrodes, respectively, and
wherein one circuit alternatively selected from the multiple source follower circuits based on the selection signal is activated.

3. The signal detection device according to claim 2, wherein each of the multiple source follower circuits includes
a first transistor, a gate of which is connected to any of the multiple electrodes associated with the source follower circuit and a drain of which is connected to a predetermined fixed potential node, and
a second transistor that is connected between a source of the first transistor and a load electric current source, the selection signal being supplied to a gate of the second transistor.

4. The signal detection device according to claim 2, wherein the amplification unit includes
a capacitor that has a first electrode that is commonly connected to output parts of the multiple source follower circuits, and an amplifier, an input part of which is connected to a second electrode of the capacitor.

5. The signal detection device according to claim 4,
wherein the amplification unit includes a transistor group for adjusting electrical characteristics of the amplifier, and
wherein one or several transistors that constitute the transistor group are selectively connected in parallel to each other to obtain minimum Ion mismatching.

6. The signal detection device according to claim 1, comprising:
multiple blocks that are arranged in the form of a matrix, and in which one block is made from the multiple electrodes, the first selection unit, and the amplification unit;
wherein the second selection unit selects an output signal of the amplification unit, which is provided to each of the multiple blocks.

7. A signal detection method for use in the signal detection device according to claim 1, the method comprising:
a selection step of causing the first selection unit to select the signals on the multiple electrodes based on the selection signal; and
an amplification step of causing the amplification unit to amplify the signal selected by the first selection unit in the selection step.

8. A method of manufacturing a signal detection device that includes a first circuit layer having flexibility, in which multiple electrode groups, each of which is made from multiple electrodes configured to come into contact with a subject that generates a signal, and multiple first selection units, each of which selects signals on the multiple electrodes based on a selection signal, are arranged in the form of a matrix, a second circuit layer having flexibility, in which multiple amplification units, each of which amplifies the signal selected by a first selection unit selected from the multiple first selection units, are arranged in the form of a matrix, and in which a second selection unit that selects a single detection signal which is output from each of the multiple amplification units that are arranged in the form of a matrix is arranged, and a conductive layer having a sheet shape that is provided between the first circuit layer and the second circuit layer, and that electrically connects between an output part of the first selection unit that is formed on the first circuit layer and an input part of an amplification unit selected from the multiple amplification units that are formed on the second circuit layer, the method comprising:
a step of stacking the first circuit layer and the second circuit layer with the conductive layer in between in such a manner that the amplification unit forms a multi-layer structure together with an electrode group that is made from the multiple electrodes and the first selection unit;
wherein the conductive layer is in the form of a sheet having anisotropic conductivity.

* * * * *